United States Patent
Kinugasa et al.

(10) Patent No.: US 11,168,420 B2
(45) Date of Patent: Nov. 9, 2021

(54) NONWOVEN FABRIC

(71) Applicant: KAO CORPORATION, Tokyo (JP)

(72) Inventors: Yoshihiko Kinugasa, Utsunomiya (JP);
Yoshihiko Seto, Utsunomiya (JP);
Masahiro Taniguchi, Utsunomiya (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 16/609,371

(22) PCT Filed: Jul. 17, 2018

(86) PCT No.: PCT/JP2018/026730
§ 371 (c)(1),
(2) Date: Oct. 29, 2019

(87) PCT Pub. No.: WO2019/044219
PCT Pub. Date: Mar. 7, 2019

(65) Prior Publication Data
US 2020/0056313 A1    Feb. 20, 2020

(30) Foreign Application Priority Data
Aug. 31, 2017  (JP) .............................. JP2017-168002

(51) Int. Cl.
*B32B 3/30*    (2006.01)
*B32B 5/02*    (2006.01)
(Continued)

(52) U.S. Cl.
CPC ............... *D04H 1/76* (2013.01); *D04H 1/74* (2013.01)

(58) Field of Classification Search
CPC ...... Y10T 428/2457; Y10T 428/24479; D04H 1/74; D04H 1/76; B32B 3/30;
(Continued)

(56) References Cited

U.S. PATENT DOCUMENTS 3,969,561 A * 7/1976 Marshall .................. B32B 5/26
428/113
4,207,367 A * 6/1980 Baker, Jr. ................. D04H 1/66
428/171
(Continued)

FOREIGN PATENT DOCUMENTS

CN        1736355 A      2/2006
CN      202415959 U      9/2012
(Continued)

OTHER PUBLICATIONS

International Search Report for PCT/JP2018/026730 dated Aug. 28, 2018.
(Continued)

*Primary Examiner* — Joanna Pleszczynska
(74) *Attorney, Agent, or Firm* — Birch, Stewart, Kolasch & Birch, LLP

(57) ABSTRACT

A nonwoven fabric 10, wherein, on a side of the one surface, a plurality of longitudinal ridge portions 11 protruding on the side of the one surface in thickness direction of the nonwoven fabric is extended in one direction Y on the side of the one surface in a plane view, and is aligned at intervals on the side of the one surface in the plane view, in other direction X, different from the one direction Y on the side of the one surface, transverse ridge portions 21 extending in the other direction X on the side of the one surface are arranged by linking the longitudinal ridge portions 11, and a fiber orientation direction in the longitudinal ridge portions 11 is different from a fiber orientation direction in the transverse ridge portions 21.

16 Claims, 15 Drawing Sheets

(51) Int. Cl.
*B32B 5/12* (2006.01)
*D04H 1/74* (2006.01)
*D04H 1/76* (2012.01)

(58) Field of Classification Search
CPC ..... B32B 5/022; B32B 5/12; A61F 13/51108; A61F 2013/51078
See application file for complete search history.

(56) References Cited

U.S. PATENT DOCUMENTS

| | | | |
|---|---|---|---|
| 2001/0053904 A1* | 12/2001 | Abuto | A61F 13/5323 604/385.101 |
| 2003/0198784 A1 | 10/2003 | Mizutani et al. | |
| 2004/0131820 A1 | 7/2004 | Turner et al. | |
| 2006/0184149 A1 | 8/2006 | Kasai et al. | |
| 2009/0105682 A1* | 4/2009 | Kouno | A61F 13/5148 604/385.04 |
| 2013/0017370 A1 | 1/2013 | Yamaguchi et al. | |
| 2013/0022784 A1 | 1/2013 | Uematsu et al. | |
| 2013/0095288 A1 | 4/2013 | Terada | |
| 2013/0158497 A1 | 6/2013 | Yamaguchi et al. | |
| 2015/0238375 A1* | 8/2015 | Nomoto | D06M 13/10 604/381 |
| 2017/0029994 A1* | 2/2017 | Ashraf | D04H 3/007 |
| 2018/0098895 A1 | 4/2018 | Hashino et al. | |

FOREIGN PATENT DOCUMENTS

| | | |
|---|---|---|
| CN | 103046232 A | 4/2013 |
| EP | 3 298 997 A1 | 3/2018 |
| JP | 2001-95845 A | 4/2001 |
| JP | 2002-23764 A | 1/2002 |
| JP | 2002-155463 A | 5/2002 |
| JP | 2006-520324 A | 9/2006 |
| JP | 2012-52253 A | 3/2012 |
| JP | 2012-136790 A | 7/2012 |
| JP | 2014-109085 A | 6/2014 |
| JP | 2015-113529 A | 6/2015 |
| TW | 201641088 A | 12/2016 |
| WO | WO 2008/146594 A1 | 12/2008 |
| WO | WO 2011/122355 A1 | 10/2011 |
| WO | WO 2011/122512 A1 | 10/2011 |
| WO | WO 2012/029391 A1 | 3/2012 |
| WO | WO 2016/104768 A1 | 6/2016 |

OTHER PUBLICATIONS

Chinese Office Action and Search Report for Chinese Application No. 201880042089.4, dated Jun. 23, 2021, with an English translation.

* cited by examiner

{FIG. 1}
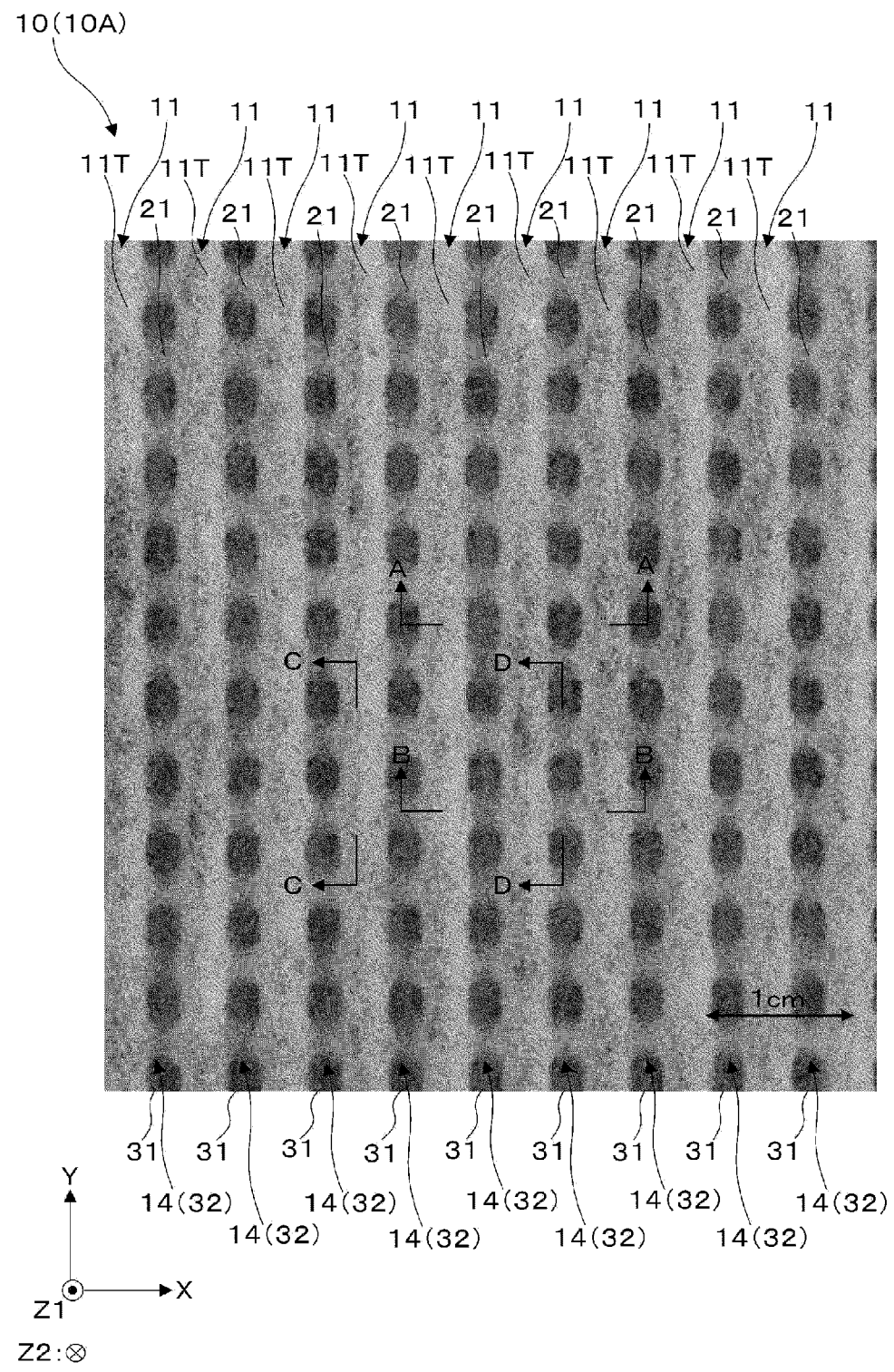

{FIG. 2}
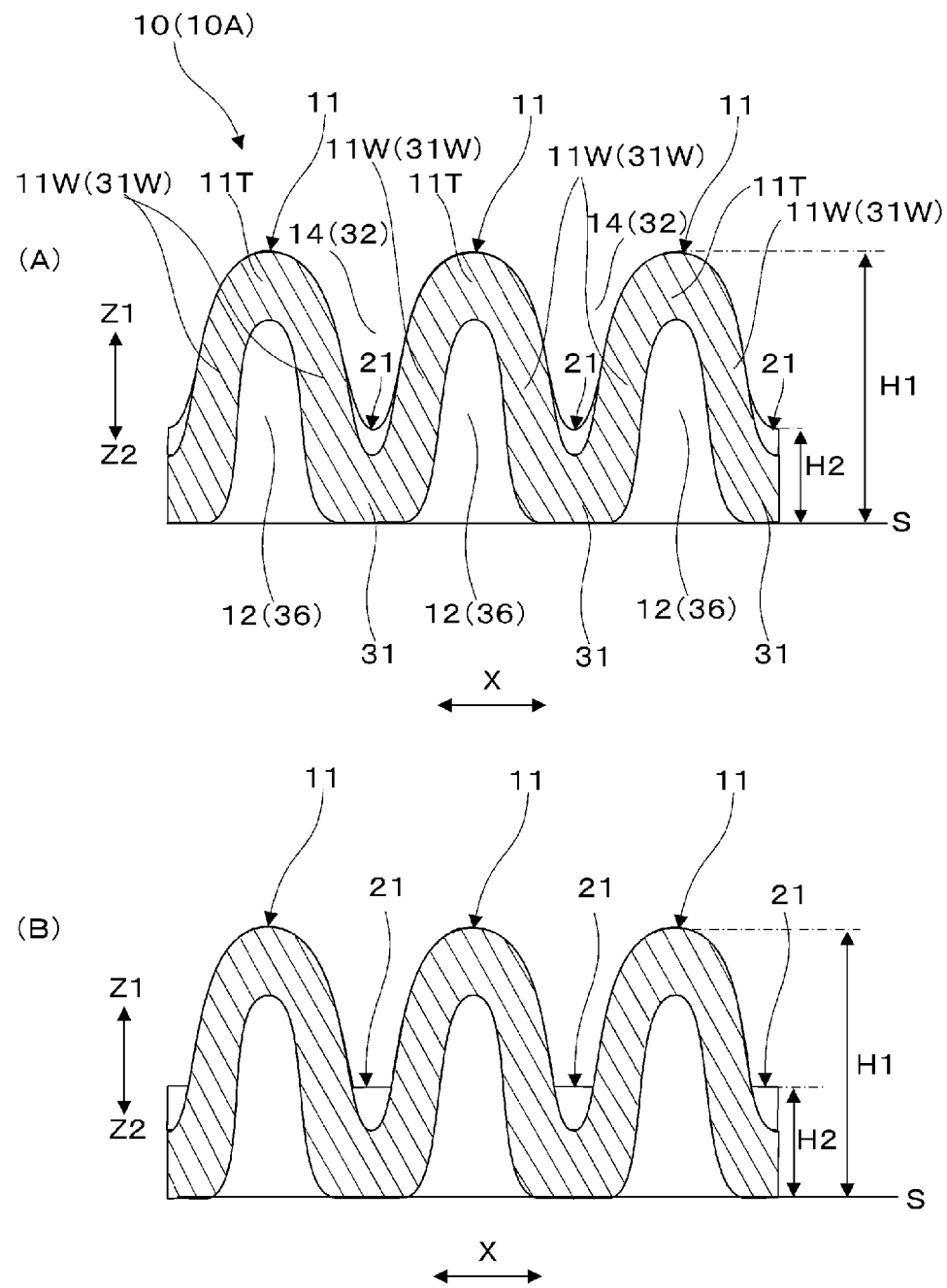

{FIG. 3}
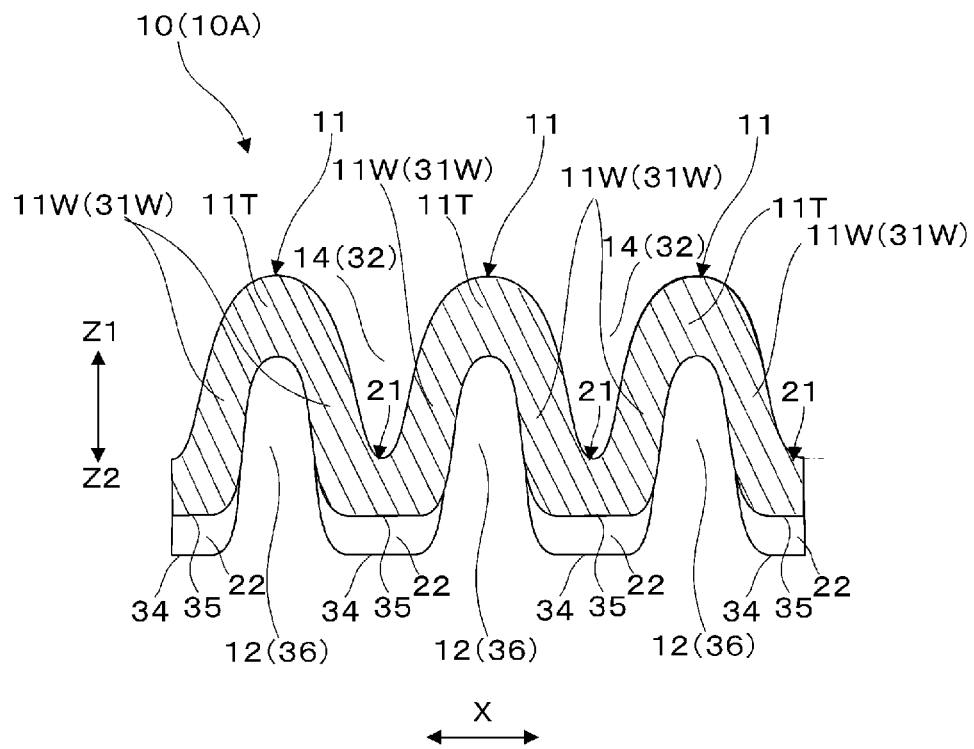
{FIG. 4}
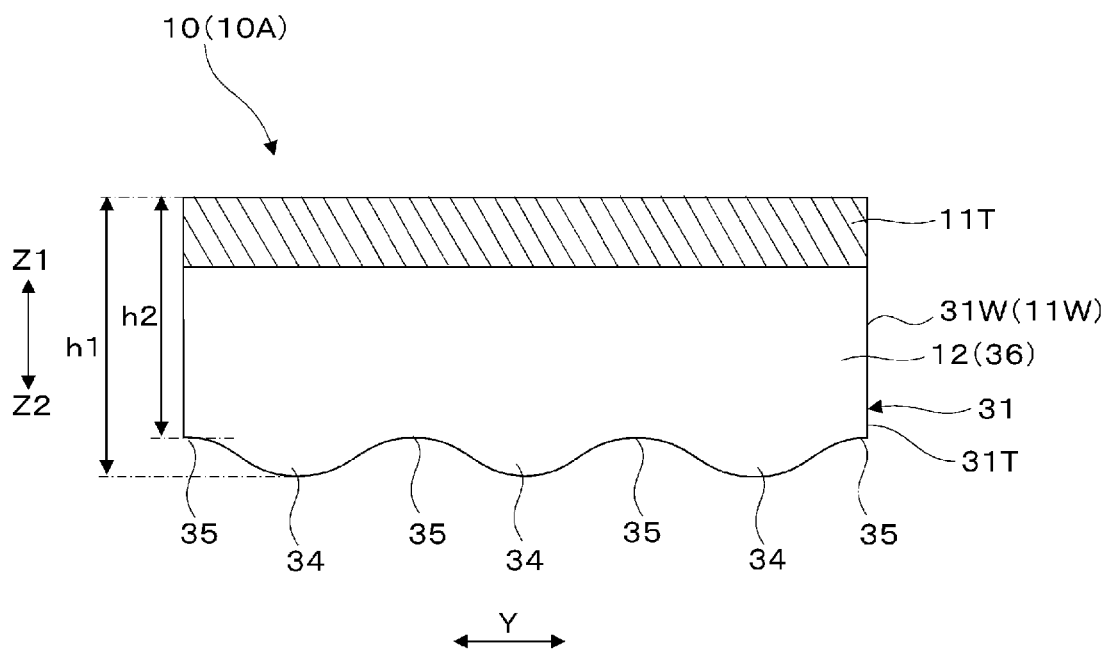

{FIG. 5}
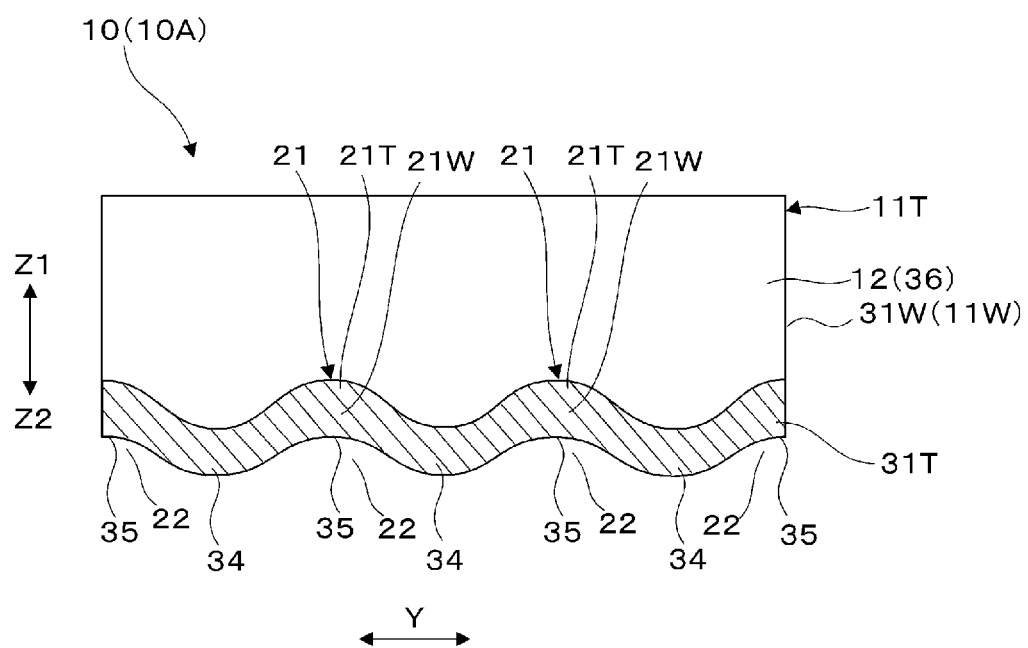

{FIG. 6}
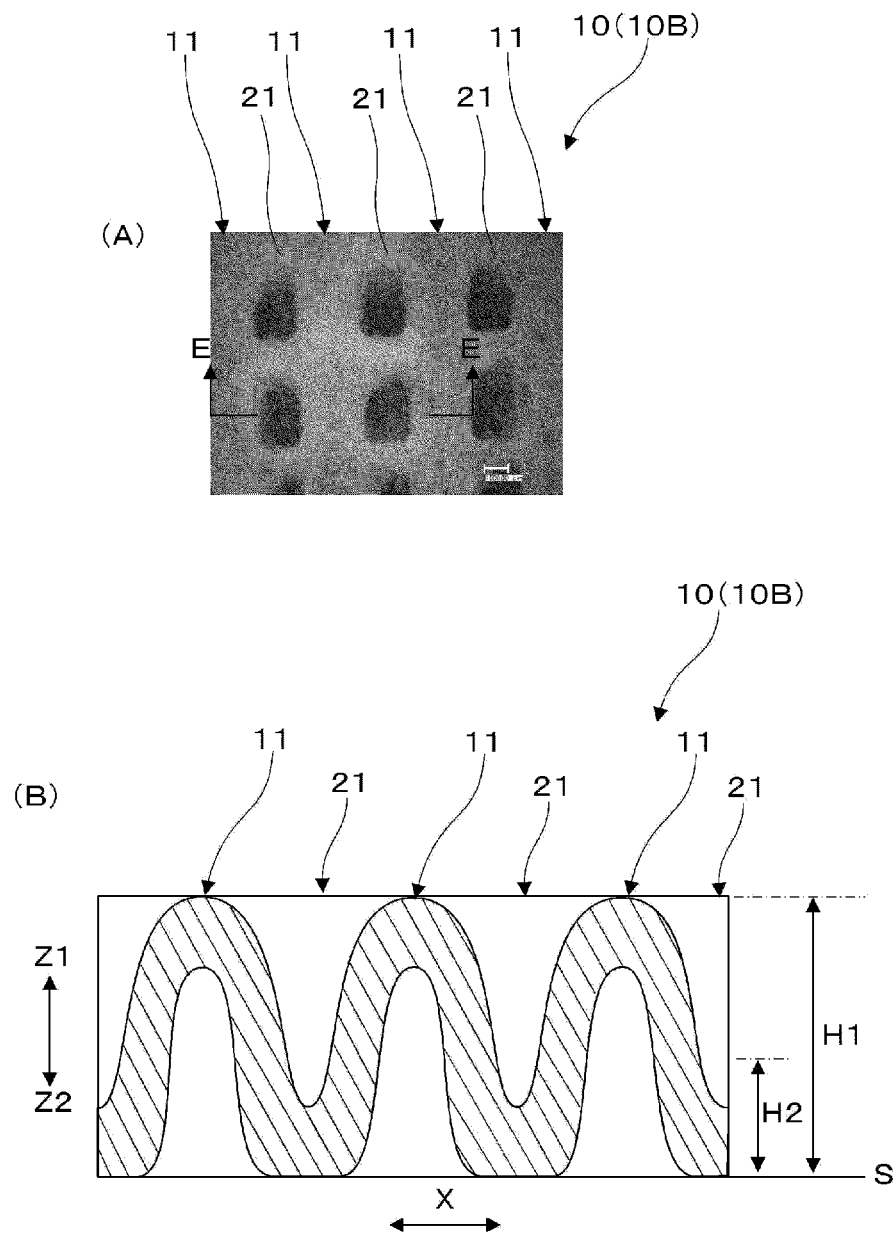

{FIG. 7}
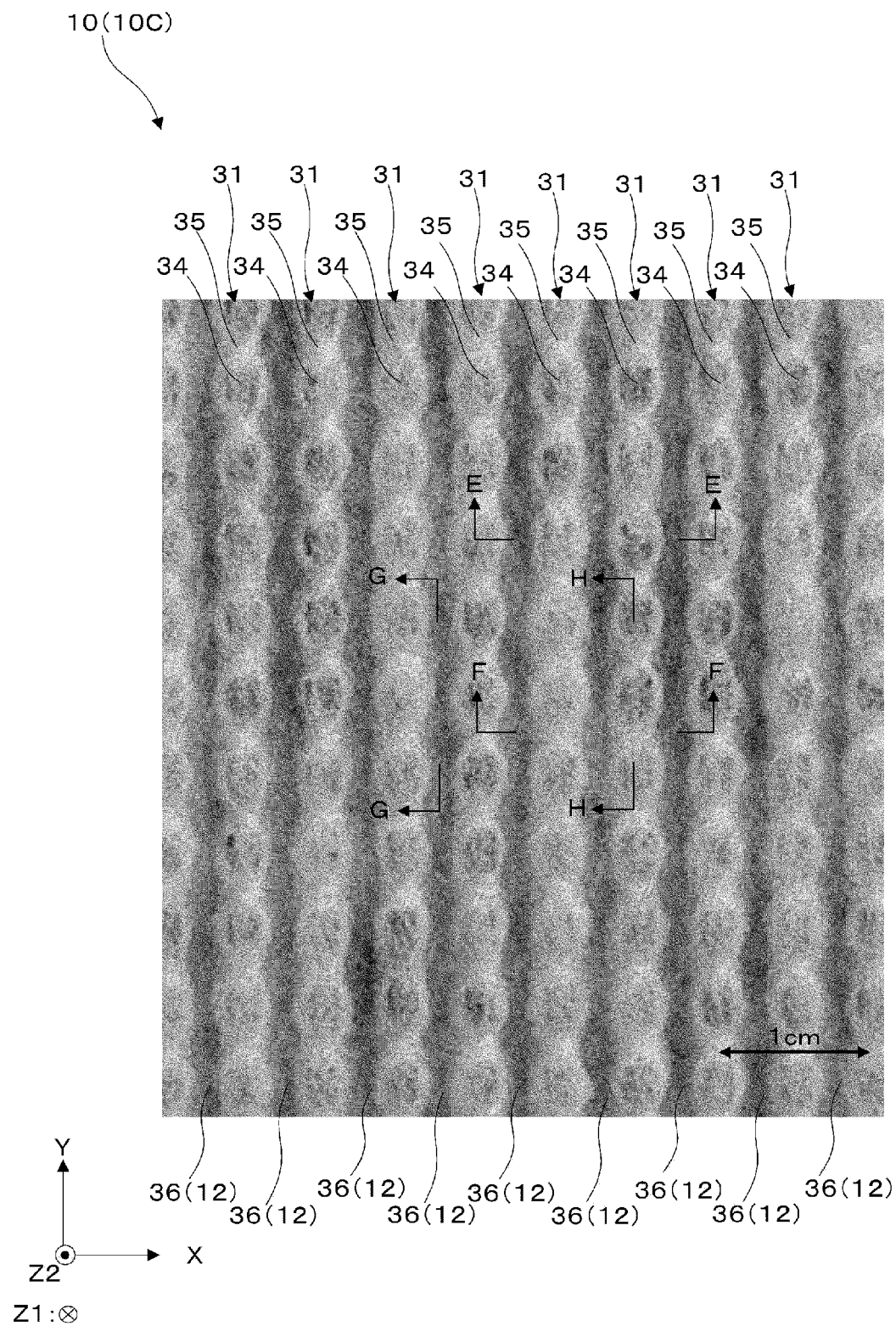

{FIG. 8}
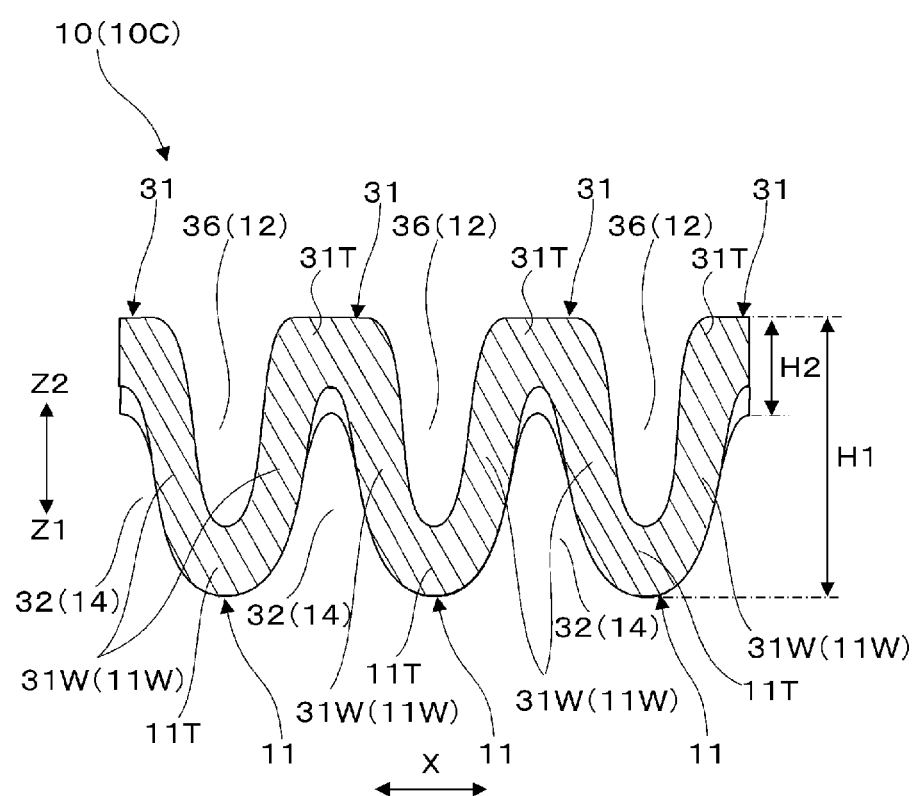

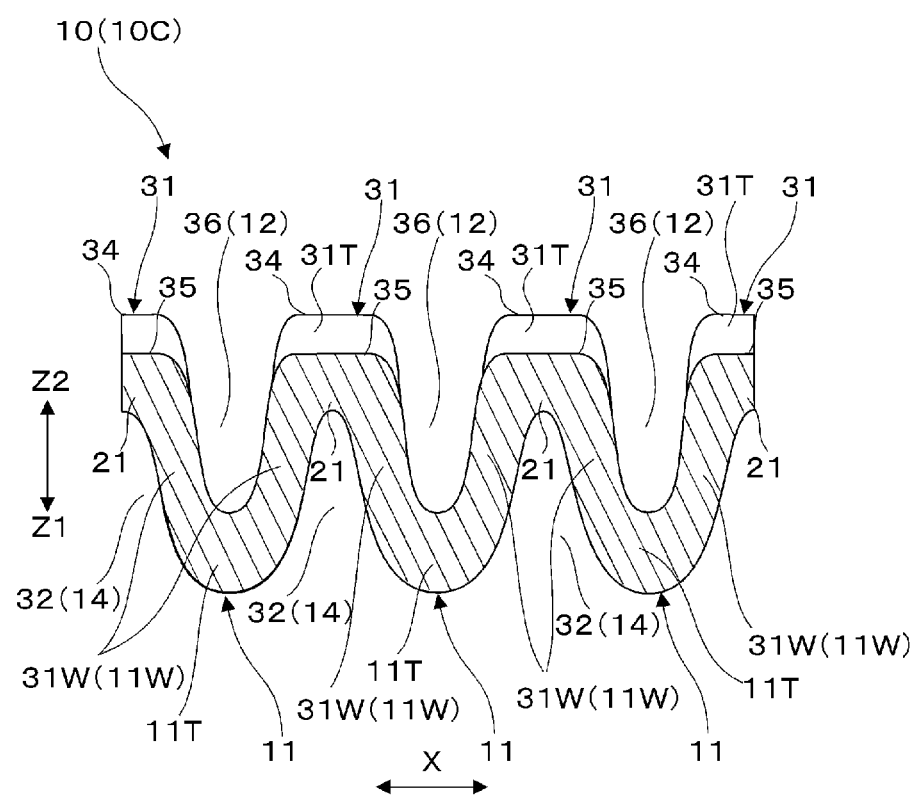
{FIG. 9}

{FIG. 10}
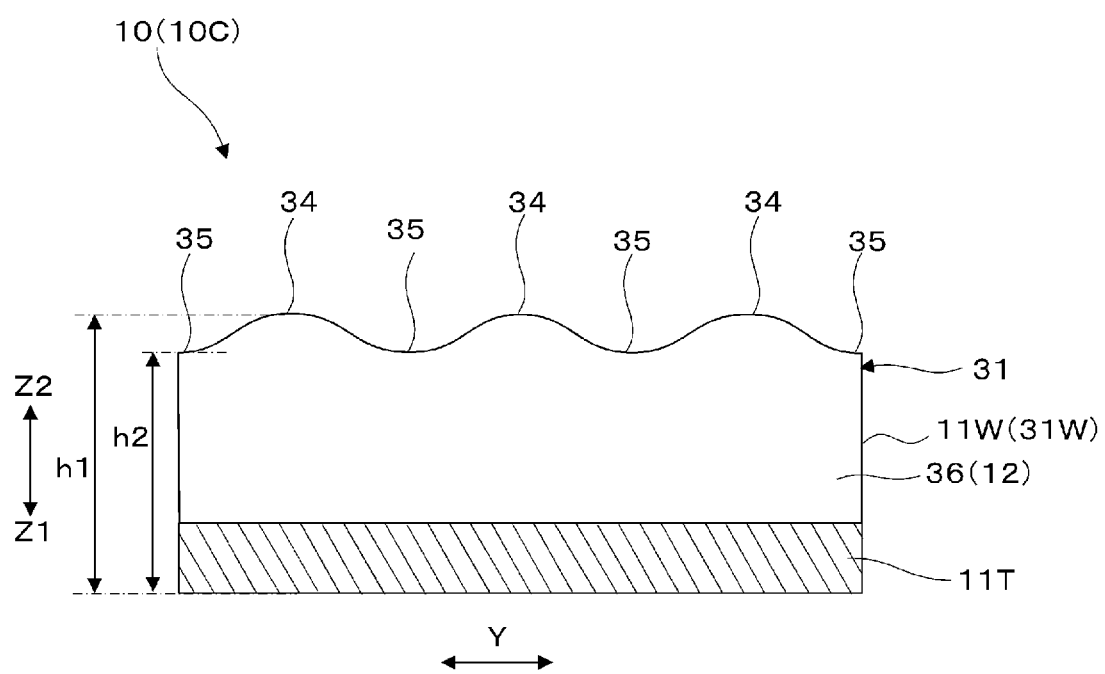

{FIG. 11}
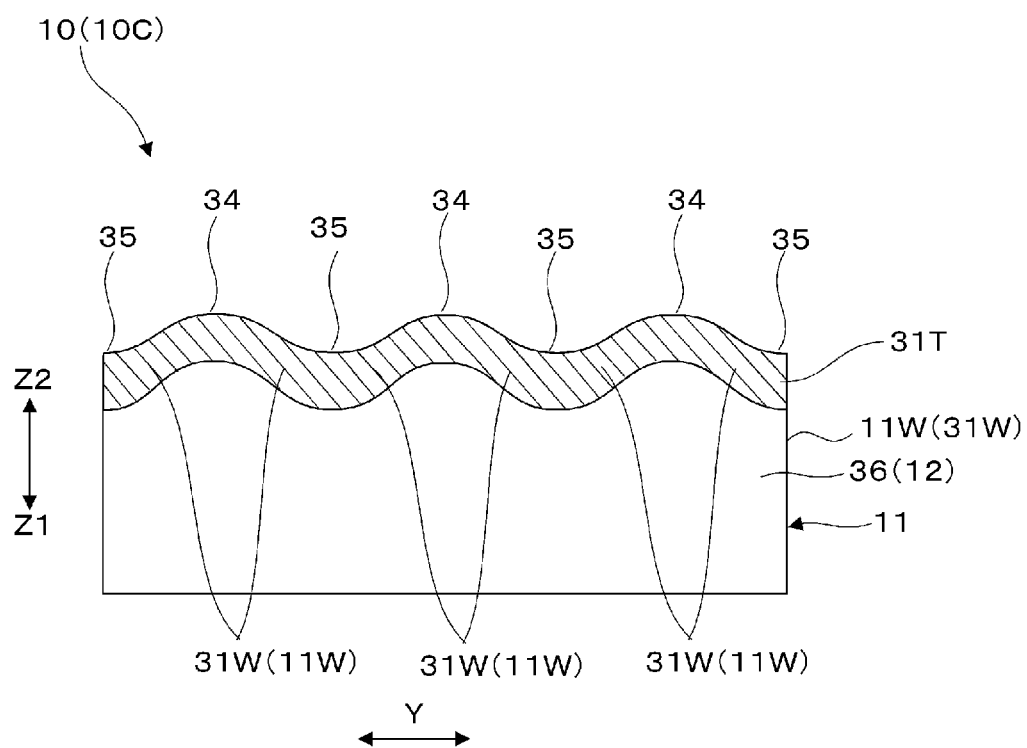

{FIG. 12}
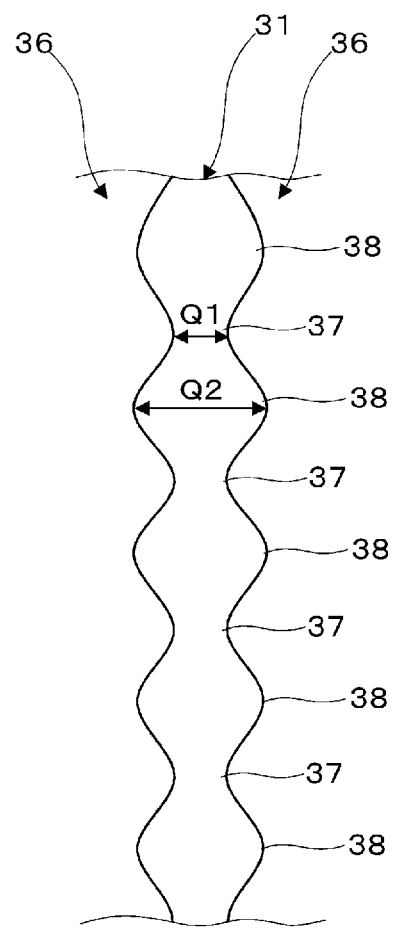

{FIG. 13}
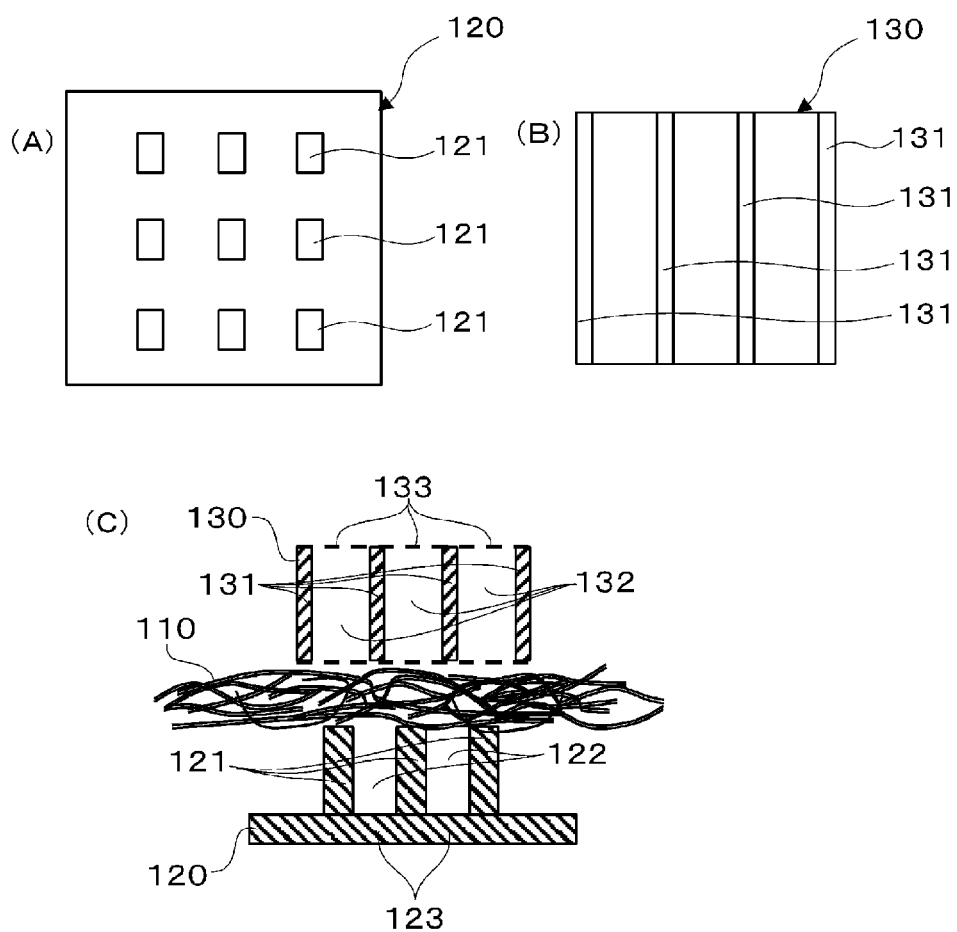

{FIG. 14}
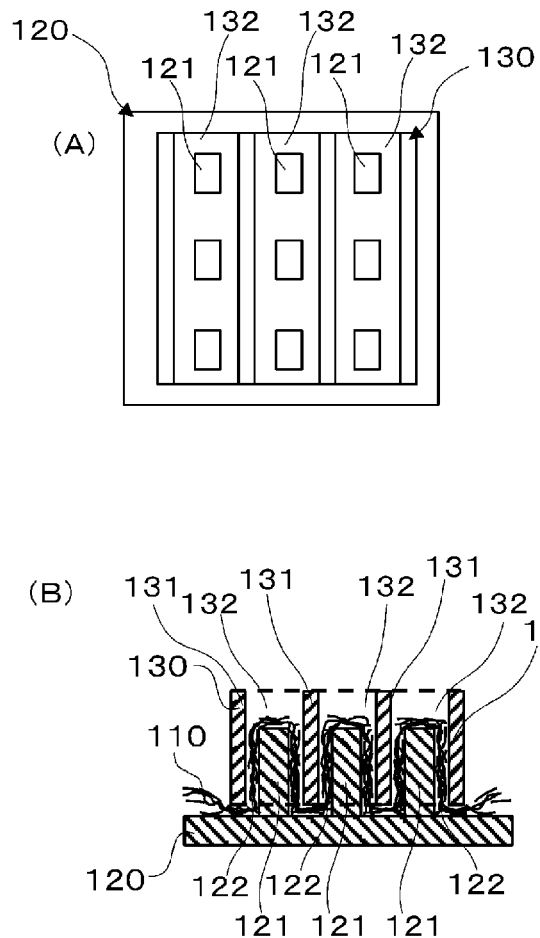
{FIG. 15}
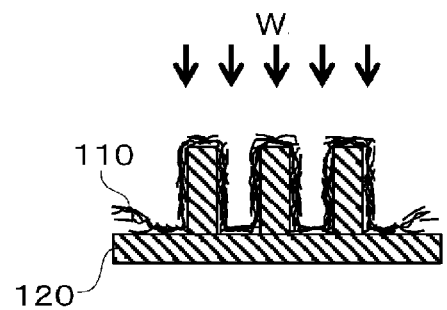

{FIG. 16}
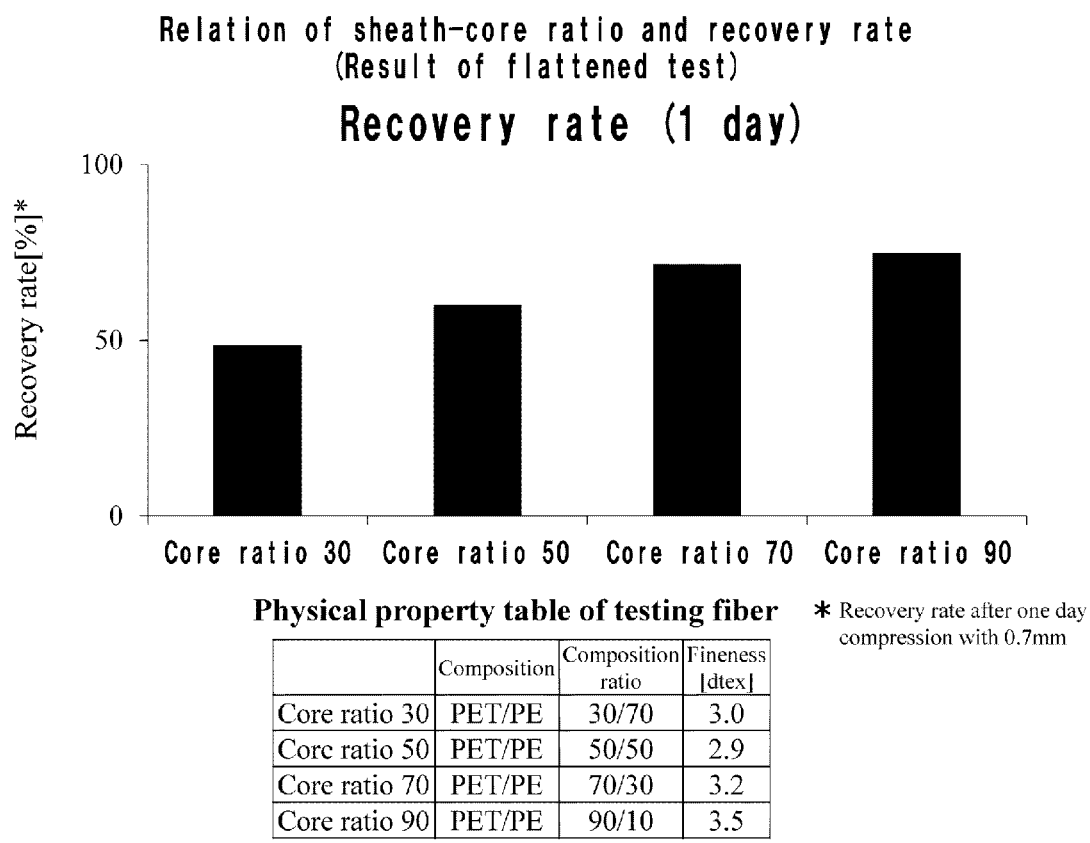

{FIG. 17}
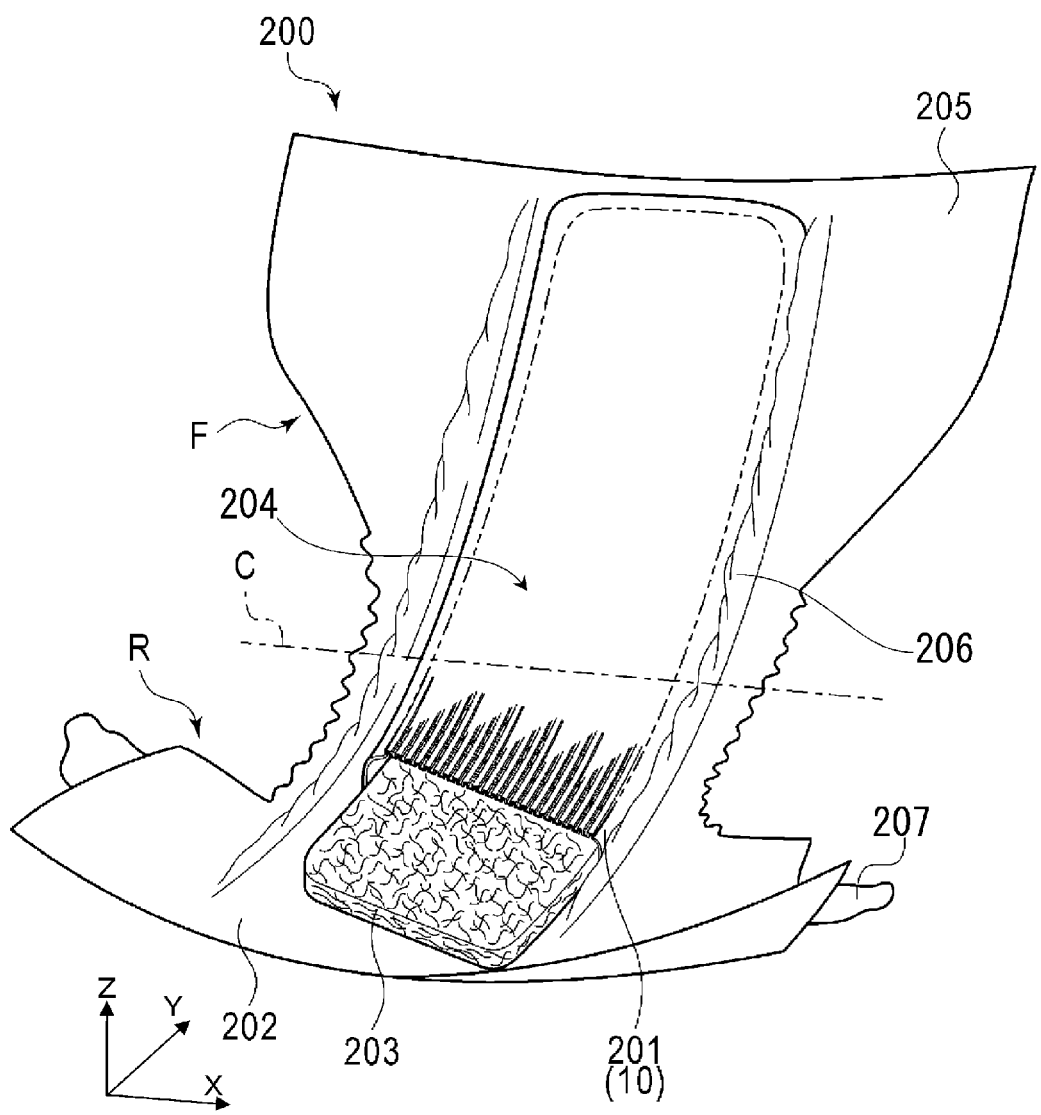

NONWOVEN FABRIC

FIELD OF THE INVENTION

The present invention relates to a nonwoven fabric.

BACKGROUND OF THE INVENTION

A nonwoven fabric is often used in an absorbent article such as a sanitary napkin or a diaper. Technology on providing this nonwoven fabric with various functions is known.

For example, Patent Literature 1 describes a composite nonwoven fabric formed of a laminated nonwoven fabric in which filaments are perpendicularly oriented, and a random nonwoven fabric in which filaments are randomly arrayed. The perpendicularly oriented laminated nonwoven fabric is formed by laminating a first nonwoven fabric and a second nonwoven fabric, both of whose filaments are arrayed and stretched in one direction, so that the directions of their filaments are perpendicular to each other. With a view to obtaining soft cushioning properties in the composite nonwoven fabric, fiber density in a first projecting portion is adjusted to be lower than fiber density in a second projecting portion.

Patent Literature 2 describes a nonwoven fabric aimed at enhancing cushioning properties and the like by processing both surfaces into concavo-convex surfaces. Specifically, Patent Literature 2 describes a concavo-convex structure in which a first projecting portion and a second projecting portion projecting in opposite directions to each other are arranged alternately in each of different directions which cross each other in a plane view through an annular wall portion. In this nonwoven fabric, with consideration to liquid-sucking properties, soft cushioning properties and the like, a wall portion has fiber orientation along a direction connecting the first projecting portion and the second projecting portion substantially at any places in a surface direction defined by a first direction and a second direction.

Moreover, Patent Literature 3 describes a topsheet of an absorbent article. In the topsheet, the nonwoven fabric is processed into a wavy shape, and a plurality of connecting portions is provided in valley portions of the wavy shape, so as to link crest portions on opposite sides of the valley portions. More specifically, the crest portions have inclined side surface portions. The connecting portions connect the inclined surfaces to each other. With consideration to shape restoration properties, the connecting portions of valley portions adjacent in crosswise direction are formed at locations offset in longitudinal direction.

CITATION LIST

Patent Literatures

Patent Literature 1: JP-A-2002-155463 ("JP-A" means unexamined published Japanese patent application)
Patent Literature 2: JP-A-2012-136790
Patent Literature 3: JP-A-2001-95845

SUMMARY OF THE INVENTION

The present invention provides a nonwoven fabric, comprising one surface and an opposite surface on a side opposite to the one surface for top and back surfaces of the nonwoven fabric, wherein, on a side of the one surface, a plurality of longitudinal ridge portions protruding on the side of the one surface in thickness direction of the nonwoven fabric is extended in one direction on the side of the one surface in a plane view, and is aligned at intervals on the side of the one surface in the plane view, in other direction, different from the one direction on the side of the one surface, transverse ridge portions extending in the other direction on the side of the one surface are arranged by linking the longitudinal ridge portions, and a fiber orientation direction in the longitudinal ridge portions is different from a fiber orientation direction in the transverse ridge portions.

Moreover, the present invention provides a nonwoven fabric, comprising one surface and an opposite surface on a side opposite to the one surface for top and back surfaces of the nonwoven fabric, wherein, on a side of the opposite surface, the nonwoven fabric comprises: a plurality of protruded line portions that is extended in one direction on the side of the opposite surface in a plane view, and is aligned at intervals in other direction on the side of the opposite surface in which the other direction is different from the one direction on the side of the opposite surface; and recessed line portions interposed between the plurality of protruded line portions, in which the recessed line portions are extended in the one direction on the side of the opposite surface, and wherein the protruded line portions are formed by connecting a plurality of convex portions in a ridge line-like shape, in which thin parts and thick parts in the plane view are alternately linked and arranged.

Other and further objects, features and advantages of the invention will appear more fully from the following description, appropriately referring to the accompanying drawings.

BRIEF DESCRIPTION OF DRAWINGS

FIG. 1 is a drawing substitute photograph showing one preferable embodiment (first embodiment) of the nonwoven fabric according to the present invention, and a photograph taken from a side of the one surface Z1 of the nonwoven fabric.

FIG. 2(A) is a partial cross-sectional view corresponding to a part in an A-A line of the nonwoven fabric shown in FIG. 1, and FIG. 2(B) is a partial cross-sectional view corresponding to a part in the A-A line of the nonwoven fabric shown in FIG. 1 when a height of a transverse ridge portion is equivalent between longitudinal ridge portions.

FIG. 3 is a partial cross-sectional view taken along a B-B line of the nonwoven fabric shown in FIG. 1.

FIG. 4 is a partial cross-sectional view taken along a C-C line of the nonwoven fabric shown in FIG. 1.

FIG. 5 is a partial cross-sectional view taken along a D-D line of the nonwoven fabric shown in FIG. 1.

FIG. 6 is a modified example of one embodiment shown in FIG. 1, in which FIG. 6(A) is a drawing substitute photograph showing a partial plane view prepared by enlarging part of a plane corresponding to FIG. 1, and FIG. 6(B) is a partial cross-sectional view showing a cross section taken along an E-E line in FIG. 2(A) corresponding to FIG. 2.

FIG. 7 is a drawing substitute photograph showing another preferable embodiment (second embodiment) of the nonwoven fabric according to the present invention, and a photograph taken from a side of the opposite surface Z2 of the nonwoven fabric.

FIG. 8 is a partial cross-sectional view taken along an E-E line of the nonwoven fabric shown in FIG. 7.

FIG. 9 is a partial cross-sectional view taken along an F-F line of the nonwoven fabric shown in FIG. 7.

FIG. 10 is a partial cross-sectional view taken along a G-G line of the nonwoven fabric shown in FIG. 7.

FIG. 11 is a partial cross-sectional view taken along an H-H line of the nonwoven fabric shown in FIG. 7.

FIG. 12 is a top view schematically showing a profile of a protruded line portion in a position half relative to an apparent thickness of a wall portion of the protruded line portion in thickness direction, viewed from a side of the opposite surface Z2.

FIG. 13 is a diagram schematically showing one example of a preferable method for producing a nonwoven fabric of the embodiment, in which FIG. 13(A) is a top view showing a support female material, FIG. 13(B) is a top view showing a support male material, and FIG. 13(C) is a cross-sectional view showing a step of disposing a fiber web on the support male material and pushing the support female material into the support male material from above the fiber web.

FIG. 14(A) is a top view showing a state in which a support male material is inserted into a support female material (however, an illustration of a web is omitted), and FIG. 14(B) is a cross-sectional view of the state described above.

FIG. 15 is a cross-sectional view showing a step of removing a support female material and blowing hot air from above a shaped fiber web to fuse fibers to each other.

FIG. 16 is a graph showing recoverability after one day compression of a nonwoven fabric in which sheath-core type conjugate fibers having core resin component of polyethylene terephthalate and sheath resin component of polyethylene are used.

FIG. 17 is a partial cutaway perspective view schematically showing a disposable diaper as one preferred embodiment of an absorbent article in which a nonwoven fabric according to the present invention is used as a topsheet.

DESCRIPTION OF EMBODIMENTS

The present invention relates to a nonwoven fabric having a large compressive deformation amount.

Methods are available for producing a nonwoven fabric having satisfactory texture, by providing the nonwoven fabric with soft cushioning properties, and specific examples include methods for securing thickness by increasing fiber amount (basis weight). However, beneficial effect on softness and flexibility of increasing fiber amount is limited, and an excessive increase in the fiber amount rather adversely affects the texture.

On the other hand, the nonwoven fabric with concavo-convex surface described in the above-described Patent Literatures can achieve thickness even if the fiber amount is small, and the texture is improved in comparison with earlier conventional flat nonwoven fabrics. However, further improvement in texture is desired.

In the invention of Patent Literature 1, the nonwoven fabric is required to be configured into three layers in order to obtain characteristics of both strength and texture, and a need is felt for improving the texture without such a configuration.

The inventions in Patent Literatures 2 and 3 are directed to realising soft cushioning properties, but leave room for texture improvement.

In a nonwoven fabric, increase in amount of compressive deformation contributes to improvement in cushioning properties and texture.

A nonwoven fabric according to the present invention is formed into a material having a large compressive deformation amount.

A preferred one embodiment (first embodiment) of the nonwoven fabric according to the present invention will be explained below, referring to FIGS. 1 to 5.

The nonwoven fabric 10 of the embodiments shown in FIGS. 1 to 5 can be applied to an absorbent article such as a disposable diaper or a sanitary napkin described later, a wiping sheet, and the like, for example. When the nonwoven fabric 10 is used in the absorbent article, the nonwoven fabric 10 is preferably used as a topsheet, and the nonwoven fabric 10 may be used by directing any surface toward a wearer's skin surface. An explanation will now be provided with consideration of an embodiment in which the nonwoven fabric 10 shown in the drawings is used with the side of one surface Z1 being toward the skin side of a user. However, the present invention should not be intended to be limited thereto.

The nonwoven fabric 10 of the embodiment has thermoplastic fibers. The nonwoven fabric 10 is formed by fusion of at least part of fibers with each other at intersections in the thermoplastic fibers, and the nonwoven fabric 10 has thickness shaped into a form different from the conventional sheet-form nonwoven fabric.

Specifically, as shown in FIGS. 1 to 5, the nonwoven fabric 10(10A) comprises top and back surfaces having one surface Z1 and an opposite surface Z2 opposite to the one surface. In the nonwoven fabric 10A, on a side of the one surface Z1 of the top and back surfaces, a plurality of longitudinal ridge portions 11 protruding in thickness direction of the nonwoven fabric 10A is extended in one direction on the side of the one surface Z1 in a plane view, and is aligned at intervals on the side of the one surface Z1 in the plane view, in other direction, different from the one direction on the side of the one surface Z1. In addition thereto, transverse ridge portions 21 are extended in the other direction on the side of the one surface Z1, and are arranged by linking the longitudinal ridge portions 11 and 11. By "linking the longitudinal ridge portions 11 and 11" is meant that the transverse ridge portions 21 adjacent to each other by interposing the longitudinal ridge portion 11 are aligned in a straight-line form. Specifically, the expression means that a deviation of a crosswise center line of the transverse ridge portion 21 and a crosswise center line of any other transverse ridge portion 21 adjacent to each other by interposing the longitudinal ridge portion 11 is within the range of a width of the transverse ridge portion 21, and for example, within 5 mm. A part surrounded by the longitudinal ridge portions 11 and the transverse ridge portions 21 is formed into a valley portion 14 recessed from a side of the one surface Z1 to a side of the opposite surface Z2.

The one direction on the side of the one surface Z1 in the nonwoven fabric 10A and the other direction on the side of the one surface Z1 in the nonwoven fabric 10A correspond to one direction (Y direction) on the side of the one surface Z1 and the other direction (X direction) crossing therewith, as shown in FIG. 1, for example. The one direction and the other direction on the side of the one surface Z1 are preferably perpendicular to each other, and more preferably a longitudinal direction and a crosswise direction of the nonwoven fabric 10A. Hereinafter, the embodiment will be described by taking the one direction in one surface Z1 as the Y direction, and the other direction as the X direction.

The longitudinal ridge portion 11 has an equivalent height along the one direction (Y direction). By "equivalent height" is meant that the height is within 0.9 times to 1.1 times a measured average value obtained by measuring height of a cross section of the nonwoven fabric by observation using a VHX900 microscope manufactured by Keyence Corporation. In addition, in the specification, all instance of the expression "height is equivalent" reflect this definition. More specifically, the longitudinal ridge portion 11 is divided into a top portion region 11T and a wall portion 11W in thickness direction of the nonwoven fabric 10, and the top portion region 11T is extended at the equivalent height in one direction (Y direction). The top portion region 11T forms an outer surface fiber layer on the side of the one surface Z1. The wall portion 11W is extended in thickness direction from the top region 11T toward the side of the opposite surface Z2. The longitudinal ridge portion 11 has an internal space 12 extending in the one direction (Y direction) inside.

The transverse ridge portion 21 is divided into a top portion region 21T and a wall portion 21W in thickness direction of the nonwoven fabric 10. The top portion region 21T is positioned on the side of the one surface Z1, and the wall portion 21W is extended in thickness direction from the top portion region 21T toward the side of the opposite surface Z2. The transverse ridge portion 21 has an internal space 22. The internal space 22 of the transverse ridge portion 21 and the internal space 12 of the longitudinal ridge portion 11 are in a state of communicating with each other on the side of the opposite surface Z2.

Further, fiber orientation direction in the longitudinal ridge portion 11 is different from fiber orientation direction in the transverse ridge portion 21. Specifically, fiber orientation direction in the top portion region 11T is different from fiber orientation direction in the top portion region 21T. By "fiber orientation direction is different" is meant that both fiber orientations obtained according to [Method for measuring fiber orientation parameter] described later intersect at an angle different by 5° or more when viewed from a top surface. When the fiber orientation is in parallel to the respective ridge portions, an angle of crosswise center lines of the ridge portions is measured by a protractor upon viewing each ridge portion from the top surface.

[Method for Measuring Fiber Orientation Parameter]

A nonwoven fabric is cut into a square of 2 cm×2 cm, a cut piece is applied as a sample, and observed from the side of the one surface Z1. A scanning electron microscope (SEM) is preferably used to the observation, for example. As the SEM, JCM-6100Plus (manufactured by JEOL Ltd.) is used, for example. In SEM observation, vapor deposition treatment is preferably applied to the sample in advance by a recommended method. A center of the longitudinal ridge portion is magnified at a magnification of 50 times, and is shown in a center of an observation screen. Next, a square having a length of 500 μm in one side with the center of the screen as an intersection of diagonal lines is drawn to be in parallel to the longitudinal ridge portion, and the number of fibers passing through two sides on both sides in parallel to an extending direction of the longitudinal ridge portion is counted (taken as the fiber number N1). Moreover, in the same manner, the number of fibers passing through two sides intersected vertically to the extending direction of the longitudinal ridge portion is counted (taken as the fiber number N2). The fiber orientation parameter in the longitudinal ridge portion is determined based on the following (Formula 1).

Fiber orientation parameter of longitudinal ridge portion (%)={Fiber number $N2$/(Fiber number $N1$+Fiber number $N2$)}×100 (Formula 1)

Such measurement is carried out on three arbitrary places, and measured values are averaged. When an average of fiber orientation parameters is more than 50%, the fibers in the region are judged to be oriented in the same direction with the extending direction of the longitudinal ridge portion, and the direction is taken as an orientation direction. A larger numerical value indicates that the fibers are strongly oriented in the same direction with the extending direction of the longitudinal ridge portion.

When a fiber orientation parameter in the transverse ridge portion is measured, in the same manner described above, a center of the transverse ridge portion is magnified at a magnification of 50 times, and is shown in a center of an observation screen. Next, a square having a length of 500 μm in one side with the center of the screen as an intersection of diagonal lines is drawn to be in parallel to the longitudinal ridge portion, and the number of fibers passing through two sides on both sides in parallel to an extending direction of the longitudinal ridge portion is counted (taken as the fiber number N1). Moreover, in the same manner, the number of fibers passing through two sides intersected vertically to the extending direction of the longitudinal ridge portion is counted (taken as the fiber number N2). The fiber orientation parameter in the transverse ridge portion with reference to the extending direction of the longitudinal ridge portion is determined based on the (Formula 1).

In order to judge whether or not the fibers in the transverse ridge portion are oriented in the same direction with the extending direction of the transverse ridge portion, a square is drawn to be in parallel to the transverse ridge portion, and not a square in parallel to the longitudinal ridge portion as in the above-described method. The number of fibers passing through two sides on both sides in parallel to the extending direction of the transverse ridge portion is counted (taken as the fiber number N3). Moreover, in the same manner, the number of fibers passing through two sides intersected vertically to the extending direction of the transverse ridge portion is counted (taken as the fiber number N4). A fiber orientation parameter (%) along the transverse ridge portion is determined, according to the method, based on the following (Formula 2), and when a value is more than 50%, the fibers are judged to be oriented in the same direction with the extending direction of the transverse ridge portion.

Fiber orientation parameter along transverse ridge portion (%)={Fiber number $N4$/(Fiber number $N3$+Fiber number $N4$)}×100 (Formula 2)

As described above, the fiber orientation direction in the top portion region 11T in the longitudinal ridge portion 11 is different from the fiber orientation direction in the top portion region 21T in the transverse ridge portion 21, and therefore when the nonwoven fabric 10A is rubbed from a certain direction, there exists an outer surface having the fiber orientation close to or along a rubbing direction. Therefore, smoother texture in a rubbing feeling can be sensed, and improvement in the texture can be realized.

Further, when a load is applied to the nonwoven fabric 10A from the side of the one surface Z1 by a skin surface (not shown), contact with the skin surface on the side of the one surface Z1 become linear contact by the longitudinal ridge portions 11, and therefore the load can be firmly supported wholly by the longitudinal ridge portions 11. Furthermore, deformation of the longitudinal ridge portion 11 in the other direction (X direction) is suppressed by the transverse ridge portion 21 linked to the longitudinal ridge portion 11, and therefore the deformation (settling) becomes hard to occur in thickness direction (Z direction) of the nonwoven fabric 10, and the shape is easily kept. Accordingly, in the nonwoven fabric 10, thickness is easily kept, and thickness is further easily increased in comparison with an ordinary concavo-convex nonwoven fabric. That is, a deformation amount is large during compression, and a cushion feeling is easily obtained. Moreover, the load is easily dispersed by different orientation directions, and the portions are hard to fall over in the same direction. More specifically, the load is easily applied vertically to a compression direction, the deformation amount is large upon touching the nonwoven fabric 10A, and the cushion feeling is further easily obtained.

On the other hand, it is preferable that, on the side of the opposite surface Z2 of the nonwoven fabric 10A, a plurality of protruded line portions 31 is extended in one direction on the side of the opposite surface Z2 in a plane view, and is aligned at intervals on the side of the opposite surface Z2 in other direction, different from the one direction of the side of the opposite surface Z2. Moreover, recessed line portions 36 interposed between the adjacent protruded line portions 31 and 31 are preferably extended in the one direction on the side of the opposite surface Z2. A plurality of the protruded line portions 31 and the recessed line portions 36 both extending in the one direction are preferably alternately arranged to form a striated concavo-convex surface. It is preferable that the nonwoven fabric 10A has an internal space 32 extending in the one direction inside the protruded line portion 31 and that the recessed line portion 36 corresponds to the internal space 12 in the longitudinal ridge portion 11 on the side of the one surface Z1 as mentioned above. For example, the one direction on the side of the opposite surface Z2 means the Y direction, and the other direction on the side of the opposite surface Z2 means the X direction. Thus, the one direction on the side of the one surface Z1 mentioned above preferably coincides with the one direction on the side of the opposite surface Z2. Hereinafter, also regarding the side of the opposite surface Z2, the embodiment will be described taking the one direction as the Y direction, and the other direction as the X direction.

The protruded line portion 31 is divided into a top portion region 31T and a wall portion 31W in thickness direction of the nonwoven fabric 10. The wall portion 31W is common to the wall portion 11W. The top portion region 31T means a part on an upper side in thickness direction (on the side of the opposite Z2), namely, on the upper side (on the side of the opposite Z2) from a center of thickness of the nonwoven fabric 10. A plurality of convex portions 34 is preferably connected in a ridge line-like shape and arranged in the top portion region 31T. Specifically, it is preferable that, in the protruded line portions 31, concave portions 35 recessed in thickness direction from the side of the opposite surface Z2 to the side of the one surface Z1 are arranged between the convex portions 34 and 34 in the extending direction, and the convex portions 34 and the concave portions 35 are alternately connected in a ridge line-like shape and arranged in the top portion region 31T to form a concavo-convex structure. In thickness direction of the nonwoven fabric 10A, height h1 of individual convex portions 34 is equivalent, and height h2 of individual concave portions 35 is substantially equivalent and is formed to be lower than the height h1. The heights h1 and h2 are heights measured from a surface of the top portion region 11T on the side of the one surface Z1 as a reference surface. By "to be lower" is meant that the height h2 is less than 0.9 times the height h1. The convex portion 34 is preferably hollow.

Thus, when the nonwoven fabric 10A is used as the topsheet of the absorbent article by disposing the side of the opposite surface Z2 having the above-described concavo-convex structure arranged in the top portion region 31T of the protruded line portion 31 on a skin-contact surface side, the convex portion 34 having the concavo-convex structure become formed into a point contact state relative to the skin surface, and the nonwoven fabric 10A therefore has excellent air permeability. Moreover, the protruded line portion 31 has an undulated shape in which a plurality of convex portions 34 is connected in a ridge line-like shape, thereby giving a comfortable bulky texture feel, in combination with the concavo-convex shape having the recessed line portions on both sides, and the nonwoven fabric 10 has a moderate elastic feel and excellent cushioning properties. From this viewpoint, as mentioned above, the convex portion 34 is preferably hollow so as to enable increased compressive deformation amount.

Further, the protruded line portions 31 preferably have thin parts and thick parts, being alternately linked.

On the side of the one surface Z1 of the nonwoven fabric 10A, the above-mentioned transverse ridge portions 21 link the longitudinal ridge portions 11 in the other direction (X direction) different from the extending direction of the longitudinal ridge portions 11, and the load applied to the longitudinal ridge portions 11 therefore is not applied to the longitudinal ridge portions 11 unevenly. Therefore, deformation of the longitudinal ridge portions 11 in the X direction is suppressed, and the longitudinal ridge portions 11 easily keep their thickness. Further, the transverse ridge portions 21 link the longitudinal ridge portions 11 in the other direction on the side of the one surface Z1, and therefore force can be uniformly dispersed in both directions. Thus, the load can be dispersed in all directions, and thickness is therefore further easily kept. Furthermore, even if the transverse ridge portions 21 are low in load bearing property respectively, the transverse ridge portions 21 can nevertheless withstand a high load because they are arranged to link the longitudinal ridge portions 11. More specifically, in the nonwoven fabric 10A, deformation is suppressed. Thus, the nonwoven fabric 10A is not easily flattened at a low load (shape-retaining properties are high), and since the nonwoven fabric 10A therefore exhibits both moderate elasticity at low load and cushioning properties in response to touching, and it achieves improved texture.

Moreover, in the nonwoven fabric 10A, if the concave portions 35 constituting the protruded line portions 31 on the side of the opposite surface Z2 are arranged opposing the transverse ridge portions 21 on the side of the one surface Z1 (FIGS. 3 to 5), the transverse ridge portions 21 become resistant to flattening even by pressing from the side of the one surface Z1, as is preferable. That is, while the longitudinal ridge portions 11 are brought into contact with a grounding surface at the convex portions 34 having the height h1 of the protruded line portions 31 on the side of the opposite surface Z2, the transverse ridge portions 21 are formed into such parts as suspended floors in the concave portions 35 each having the height h2 of the protruded line portion 31 on the side of the opposite surface Z2, whereby deformation by the grounding surface is suppressed.

From a viewpoint of the above-described deformation suppression, a plurality of the transverse ridge portions 21 is preferably aligned at intervals in one direction (Y direction) on the side of the one surface Z1, namely, the extending direction of the longitudinal ridge portion 11 with linking the longitudinal ridge portions 11 and 11 in the other direction (X direction) on the side of the one surface Z1.

The nonwoven fabric 10A preferably has a lattice-shaped concavo-convex surface on the side of the one surface Z1 by the longitudinal ridge portions 11 and the transverse ridge portions 21. By "lattice-shaped" herein is meant that the longitudinal ridge portions and the transverse ridge portions form a shape having lattice points and sides in the plane view, and the shape includes various lattice shapes such as a triangular lattice and a hexagonal lattice without being limited a tetragonal lattice. When the X direction and the Y direction on the side of the one surface Z1 are perpendicular, the ridge portions formed of the longitudinal ridge portions 11 and the transverse ridge portions 21 are arranged in a perpendicular lattice form, when viewed from the side of the one surface Z1. Hereinafter, the "ridge portion" means both the longitudinal ridge portions 11 and the transverse ridge portions 21. The ridge portions are formed into the lattice form, and therefore when the load is applied to the nonwoven fabric 10A from the side of the one surface Z1, the load applied to the longitudinal ridge portions 11 is dispersed into the transverse ridge portions 21.

Further, in the nonwoven fabric 10A, the fiber orientation direction in the longitudinal ridge portions 11 on the side of the one surface Z1 and the fiber orientation direction in the transverse ridge portions 21 on the side of the one surface Z1 are preferably directed toward the extending direction of the ridge portions, respectively. That is, fiber orientation direction in the longitudinal ridge portions 11 is preferably directed in the Y direction (the one direction) on the side of the one surface Z1, and fiber orientation direction in the transverse ridge portions 21 is preferably directed in the X direction (the other direction) on the side of the one surface Z1. By a "directed" in the specification is meant that a difference in the direction between the orientation direction obtained according to the method for measuring fiber orientation parameter as mentioned above, and the extending direction of the ridge portion is less than 5°.

If each ridge portion has fiber orientation direction as described above, the shape-retaining properties, the elasticity, cushioning properties and the like of the nonwoven fabric 10A as mentioned above are further enhanced. That is, when the load is applied to the longitudinal ridge portions 11, and the longitudinal ridge portions 11 are about to be flattened, the load is dispersed in the orientation direction of constituent fibers of the transverse ridge portions 21, and the longitudinal ridge portions 11 are suppressed from being deformed in the crosswise direction (X direction) by the transverse ridge portions 21. Thus, excessive deformation of the longitudinal ridge portions 11 in the crosswise direction is suppressed, thickness of the longitudinal ridge portions 11 is maintained, and the shape-retaining properties, the elasticity, cushioning properties and the like of the nonwoven fabric 10A are further enhanced.

As described above, the nonwoven fabric 10A has a structure having the longitudinal ridge portions 11 and the transverse ridge portions 12 as mentioned above on the side of the one surface Z1, and thus the nonwoven fabric 10A is formed into a material having the moderate elastic feeling, and excellent soft cushioning properties. Moreover, the nonwoven fabric 10A is formed into a material keeping unprecedented comfortable bulkiness, and having satisfactory texture. These characteristics are further enhanced by a configuration having the protruded line portions 31 and the recessed line portions 36 on the side of the opposite surface Z1.

(Method for Measuring Compressive Deformation Amount)

The above-described characteristics of the nonwoven fabric 10A can be evaluated by the following measurement. That is, all of compressive characteristics up to 5.0 kPa are evaluated in a normal mode by KES-FB3 (trade name) manufactured by Kato Tech Co., Ltd. except that a terminal speed is set to 0.1 mm/s. Then, an amount deformed from 0.15 kPa to 2.5 kPa is taken as "compressive deformation amount" of the nonwoven fabric 10A. The elasticity and cushioning properties are judged based on "the compressive deformation amount". The larger level of this numerical value indicates that the nonwoven fabric is harder to be flattened in the compression direction by the small load, and moderately has elasticity in the same manner. Moreover, the larger level of this numerical value indicates that the nonwoven fabric 10A is easily flattened during a load of 2.5 kPa, and if the numerical value is large, the nonwoven fabric 10A is significantly deformed upon touching the nonwoven fabric 10A, and therefore cushioning properties are easily felt.

Moreover, the longitudinal ridge portions 11 and the transverse ridge portions 21 in which the fibers are oriented in the extending direction of the ridge portion respectively have action of improving the texture, as mentioned above, because fiber orientation directions are different between the top portion regions 11T and 21T in each ridge portion. When the texture is confirmed, a person performs rubbing operation in addition to pushing operation. In this case, smoother texture is realized by existence of the outer surface having orientation along the rubbing direction. Thus, an unprecedented feeling is realized by having smoothness produced by the fiber orientations in the extending directions of the ridge portions and the cushion feeling in thickness direction of the longitudinal ridge portions 11.

Moreover, the shape-retaining properties and the cushion feeling are high in the nonwoven fabric 10A. Therefore, for the reason of a wide space and capability of efficiently migrating urine into an absorbent body upon injecting the liquid such as urine thereinto, liquid spreading is also further narrowed in shreds.

In a method for measuring the liquid spreading, Merries Tape S size, manufactured by Kao Corporation, 2016, is used, and a top material and a sublayer are peeled by a cold spray, and a measuring object nonwoven fabric is placed thereon. Then, 40 mL of colored artificial urine is injected thereinto for 4 seconds, and the resultant material is allowed to stand for 10 minutes, and the operation is repeated 4 times in total. Then, an OHP sheet is placed on the surface material to surround a part in which coloring remains. An area surrounded is measured, and the resultant value is taken as the liquid spreading. In addition, as the artificial urine, a material blended in a proportion of 1.940 mass % of urea, 0.795 mass % of sodium chloride, 0.110 mass % of magnesium sulfate, 0.062 mass % of calcium chloride, 0.197 mass % of potassium sulfate, 0.010 mass % of red No. 2 (dye), water (about 96.88 mass %) and polyoxyethylene lauryl ether (about 0.07 mass %), in which the surface tension is adjusted to 53±1 mN/m (23° C.), is used.

Further, in the nonwoven fabric 10A, as shown in FIG. 2(A), when the side of the opposite surface Z2 of the nonwoven fabric 10A is placed on a plane S, a height H1 of the longitudinal ridge portion 11 and a height H2 of the transverse ridge portion 21 are preferably different, for example. The height H1 of the longitudinal ridge portion 11 is more preferably higher than the height H2 of the transverse ridge portion 21. At this time, in the transverse ridge portion 21, the height may be changed along the X direction between the longitudinal ridge portions 11 and 11. For example, the transverse ridge portions 21 are preferably arranged in a bent state into a concave form in such a manner that the transverse ridge portions 21 are recessed in the direction on the side of the opposite surface Z2 between the longitudinal ridge portions 11 and 11. In other words, a cross-sectional shape obtained by cutting the transverse ridge portion 21 along the Y direction preferably has an inverted U-shape having thickness, and is formed into a shape such as a so-called saddle used for a horse. As shown in FIG. 2(A), the height of the transverse ridge portion 21 in this case corresponds to a height at the lowest portion (or a part in which a curvature becomes largest) bent in the concave shape. Alternatively, as shown in FIG. 2(B), the transverse ridge portion 21 may have an equal height between the longitudinal ridge portions 11 and 11. The plane S means a plane on which the side of the opposite Z2 of the nonwoven fabric 10 is placed on a flat surface.

When the nonwoven fabric 10 is viewed from the side of the opposite surface Z2, the concave portions 35 are to be arranged in parts corresponding to the transverse ridge portions 21 between the protruded line portions 31 by adjusting the height H1 of the longitudinal ridge portion 11 to be higher than the height H2 of the transverse ridge portion 21, and therefore the space is widened on the side of the opposite surface Z2. Thus, when dust is tried to be collected on the side of the opposite surface Z2 by using the nonwoven fabric 10A as a wiping sheet, a collection space is widened by a space formed by disposing concave parts in the protruded line portions 31, and a dust collection amount is increased and a dust collection effect is enhanced.

Moreover, when the nonwoven fabric 10 is used as the surface material of the absorbent article by applying the side of the one surface Z1 as the skin surface, a site in contact with the skin is only a part of the height H1, even if the liquid remains, by adjusting the height H1 of the longitudinal ridge portion 11 to be higher than the height H2 of the transverse ridge portion 21, and therefore from viewpoints of liquid remain and air permeability, the nonwoven fabric 10 is further friendly to the skin.

The transverse ridge portion 21 has a configuration recessed therein as mentioned above. Thus, both end portions of the concave portion 35 have, on the side of the opposite surface Z2, such strength as capable of keeping a concave portion shape. This reason is that, when a load is applied to the longitudinal ridge portions 11, the load is first applied to both end portions of the concave portions 35 of the transverse ridge portions 21 in the nearest position, but the nonwoven fabric 10A has strength capable of keeping the concave portion shape, and therefore can receive the load from the longitudinal ridge portions 11. Thus, the shape can be easily kept and moderate elasticity can be provided. Further, the shape is easily kept, and therefore the internal space of the transverse ridge portion 21 is kept, and when the nonwoven fabric 10 is used as the surface material of the absorbent article, the liquid spreading is minimized. Furthermore, the liquid flows along the concave portions 35 to enhance absorption.

Next, a modified example of the first embodiment will be explained below, referring to FIG. 6. In addition, the same sign is placed to the same component as the component in the nonwoven fabric 10A according to the first embodiment.

Specifically, as shown in FIG. 6, a nonwoven fabric 10(10B) is a material in which transverse ridge portions 21 are arranged at a height equal to a height of longitudinal ridge portion 11 in the above-mentioned nonwoven fabric 10A. The nonwoven fabric 10(10B) has the same configuration as the above-mentioned nonwoven fabric 10A except the height of the transverse ridge portion 21. In this nonwoven fabric 10б, the height of the transverse ridge portion 21 on a side of the one surface Z1 is high, and therefore an internal space of the transverse ridge portion 21 existing on the side of the opposite surface Z2 is widened, and the liquid spreading is further minimized in association therewith. Moreover, the nonwoven fabric 10B has a feature of a high dust collection effect.

Next, another preferred embodiment (second embodiment) of the nonwoven fabric according to the present invention will be explained below, referring to FIGS. 7 to 11. In addition, the same sign is placed to the same component as the component in the nonwoven fabric 10A according to the first embodiment.

As shown in FIGS. 7 to 11, the nonwoven fabric 10(10C) comprises top and back surfaces having one surface Z1 and an opposite surface Z2 opposite to the one surface.

In the nonwoven fabric 10C, on the side of the opposite surface Z2 of top and back surfaces, a plurality of protruded line portions 31 is extended in one direction on the side of the opposite surface Z2 in the plane view, and are separated from each other and arranged in alignment in the other direction on the side of the opposite surface Z2, different from one direction on the side of the opposite surface Z2. Moreover, the recessed line portion 36 interposed between adjacent protruded line portions 31 and 31 is extended in one direction on the side of the opposite surface Z2. The plurality of protruded line portions 31 and the recessed line portions 36 both extending in one direction are alternately arranged to form the same streaked concavo-convex surface as the surface of the above-mentioned nonwoven fabric 10A. The nonwoven fabric 10C has the above-described internal space 32 extending in one direction inside the protruded line portion 31. In the internal space 32, a part in which the height is high and a part in which the height is low relative to one direction alternately repeatedly exist. For example, as shown in FIG. 7, one direction on the side of the opposite surface Z2 corresponds to the Y direction, and the other direction on the side of the opposite surface Z2 corresponds to the X direction. Moreover, the Y direction and the X direction are preferably perpendicular to each other, and are more preferably a longitudinal direction and a crosswise direction of the nonwoven fabric 10C, respectively. Also in the embodiment, hereinafter, the embodiment will be described by taking one direction as the Y direction, and the other direction as the X direction.

In the nonwoven fabric 10C, in the same manner as the above-mentioned nonwoven fabric 10A, the protruded line portion 31 is divided into a top portion region 31T and a wall portion 31W in thickness direction of the nonwoven fabric 10. In the top portion region 31T, the convex portions 34 and the concave portion 35 are alternately connected ridge line-like and arranged to form the concavo-convex structure, and the same effect as in the above-mentioned nonwoven fabric 10A is produced. The convex portion 34 is preferably hollow, and the compressive deformation amount can be increased by the hollowness.

As shown in FIG. 12, in the protruded line portion 31, thin parts 37 and thick parts 38 are preferably alternately linked and arranged. The width of the protruded line portion 31 means a width measured in the thickest position interposed with the wall portions 31W to the center of thickness, when viewed from the top surface of the wall 31W of the protruded line portion 31 in view from the side of the opposite surface Z2. The thinnest portion 37 of the protruded line portion 31 of measured widths is taken as a width Q1, and the thickest portion 38 of the protruded line portion 31 is taken as a width Q2.

The thin part 37 and the thick part 38 in the protruded line portion 31 create two elements, which are softness and difficulty in being flattened with the low load, by alternately comprising a thick part having softness in which the fiber density is low, and a thin part having high resistance to compression in which the fiber density is high.

In such a nonwoven fabric 10C, when the side of the opposite surface Z2 of the nonwoven fabric 10C is rubbed with a finger, soft texture can be felt by touching the protruded line portions 31 in which the thin parts 37 and the thick parts 38 are alternately linked and arranged. The thin part 37 and the thick part 38 preferably correspond to the above-mentioned concave portion 35 and convex portion 34, respectively.

Moreover, in the nonwoven fabric 10C of the second embodiment on a side of the one surface Z1, a plurality of longitudinal ridge portions 11 and transverse ridge portions 21 is preferably arranged to the side of the one surface Z1. It is preferable that the longitudinal ridge portions 11 are formed into projections having a predetermined height H1 in thickness direction of the nonwoven fabric 100, and are extended in one direction on a side of the one surface Z1 in the plane view, and are separated from each other and arranged in alignment in the other direction in the plane view on a side of the one surface Z1, different from one direction on a side of the one surface Z1. It is preferable that this longitudinal ridge portion 11 has the above-described internal space 12 extending in one direction inside thereof, and the internal space 12 corresponds to the recessed line portion 36.

In the same manner as the nonwoven fabric 10A, in the nonwoven fabric 10C, it is preferable that the fiber orientation direction constituting the longitudinal ridge portions 11 is different from the fiber orientation direction constituting the transverse ridge portions 21, and that the fiber orientation direction is directed toward the extending direction of each ridge portion.

In the nonwoven fabric 10C, the configuration on a side of the one surface Z1 is preferably the same as the configuration in the above-mentioned nonwoven fabric 10A. For example, the nonwoven fabric 100 preferably has the lattice-shaped concavo-convex surface on a side of the one surface Z1 by the longitudinal ridge portions 11 and the transverse ridge portions 21. When the load is applied to such a nonwoven fabric 10C from the side of the opposite surface Z2, the protruded line portions 31 are hard to be flattened when the load is low due to an influence of the thin parts 37 formed by the transverse ridge portions 21, and has the moderate elasticity. Further, when the load is applied thereto from the side of the opposite surface Z2 on which the protruded line portions 31 are arranged and the protruded line portions 31 are about to be flattened, the protruded line portions 31 are difficult in falling over in the same direction, and therefore the texture is improved because the protruded line portions 31 have the moderate elasticity and cushioning properties. Furthermore, in the protruded line portions 31 in this case, bottom portions of the concave portions 35 are supported by the transverse ridge portions 21 linking the recessed line portions 36 being adjacent sites (FIGS. 8 and 9). Therefore, in the protruded line portions 31, the thickness further easily remains in the concave portion 35 in comparison with the convex portion 34 having no transverse ridge portions 21. Thus, when the nonwoven fabric 10C is pressed from the side of the opposite surface Z2, a soft cushion feeling induced by the convex portions 34 and the comfortable texture induced by the concave portions 35 can be further sensed.

As described above, the nonwoven fabric 10C has the above-mentioned structure having the protruded line portions 31 and the recessed line portions 36 on the side of the opposite surface Z2, and therefore is formed into a material having the moderate elastic feeling and the excellent soft cushioning properties and the satisfactory texture in the same manner as the nonwoven fabric 10. These characteristics are further enhanced by the configuration having the longitudinal ridge portions 11 and the transverse ridge portions 21 on a side of the one surface Z1.

In the nonwoven fabrics 10A to 10C, each of two lines forming a profile of the protruded line portion 31 in the crosswise direction in the plane view from the side of the opposite surface Z2 is preferably a curve having a plurality of arcs. More specifically, the curve is a smooth and continuous line formed of connecting the arcs by alternately changing orientations of the convex portions of the arc in an opposite direction.

In the nonwoven fabric 10 having the above-described configuration, the side portion of the protruded line portion 31 is formed into the curve having the arc, and therefore the feeling in touching the side of the opposite surface Z2 of the nonwoven fabric 10 is sensed to be softer than a feeling in the case of a straight line. Therefore, the texture is felt to be satisfactory.

The nonwoven fabrics 10A to 10C preferably comprise fluff on the side portion of the protruded line portion 31.

The fluff is in a state in which the fibers are not fused, and one end of the fibers comes out from the protruded line portions 31. The fibers are not fused, and when the nonwoven fabric is compressed and cushioning properties are felt, a feeling enveloped by the fibers can be obtained. Presence of the fluff on the ridge portion and the side portion of the convex portion can induce improvement in such a soft feeling as being enveloped.

The nonwoven fabric 10 having the above-described configuration can keep the apparent thickness (bulkiness) and the comfortable softness of the nonwoven fabric 10 even during absorbing the pressing force. That is, deep sinking is induced in a limited range of the nonwoven fabric 10, and a three-dimensional structure of the nonwoven fabric 10 as a whole is kept. Further, the nonwoven fabric 10 has the fluff on the side portion of the protruded line portion 31. Thus, such a feeling as being enveloped by a thick nonwoven fabric is obtained in a periphery of the pressing finger. Texture is reputedly felt not only in a ball of the finger but also in the periphery thereof (Transactions of the Virtual Reality Society of Japan Vol. 9, No. 2, 2004, Display of Soft Elastic Object by Simultaneous Control of Fingertip Contact Area and Reaction Force). Therefore, it is considered that the nonwoven fabric is felt to have further satisfactory texture by the feeling in which the whole is enveloped.

Thus, the nonwoven fabric 10 has the fluff on the side portion of the protruded line portion 31, and upon pressing the nonwoven fabric 10 with the finger, softness of the fluff is sensed around the finger, and nonwoven fabric 10 can be sensed to have excellent texture.

Moreover, in the above-described nonwoven fabric 10 having the fluff, the fluff catches the dust, and therefore the dust collection effect is enhanced.

In the nonwoven fabric 10, the longitudinal ridge portions 11 and the valley portions 14, the transverse ridge portions 21 and the valley portions 14, the protruded line portions 31 and the recessed line portions 36, the longitudinal ridge portions 11 and the transverse ridge portions 21 and the like are united to each other without seam, in which at least part of the fibers are fused to each other. As described above, the nonwoven fabric 10 is formed into a material having bulkiness and thickness by linking each site to support the site. The thickness of the nonwoven fabric 10 means an apparent thickness in a shaped form of the nonwoven fabric as a whole, and not a thickness in a local of the longitudinal ridge portions 11, the protruded line portions 31 or the transverse ridge portions 21.

In addition, in the nonwoven fabric 10, also in each site other than a connection part between the respective sites, the thermoplastic fibers are fused to each other at the intersections of at least part of the fibers with each other. The nonwoven fabric 10 may have the intersections in which the thermoplastic fibers are not fused to each other. Moreover, the nonwoven fabric 10 may contain fibers other than the thermoplastic fibers, and such cases include ones where the thermoplastic fibers are fused at the intersections with the fibers other than thermoplastic fibers.

The nonwoven fabric 10 is formed into a material having the thickness (bulkiness) enough to provide the product with cushioning properties by the three-dimensional structure in thickness direction without increasing a fiber amount. Therefore, the nonwoven fabric 10 has higher flexibility, and is further easily bent without resistance upon being bent than a material provided with the thickness by merely increasing the fiber amount. Further, the nonwoven fabric 10 is superb in the texture by the above-described fiber orientation.

In the nonwoven fabric 10, from a viewpoint of providing the nonwoven fabric 10 with excellent flexibility and cushioning properties, the apparent thickness and the basis weight are preferably within the following range.

From a viewpoint of ensuring cushioning properties, the apparent thickness of the nonwoven fabric is preferably 1.5 mm or more, more preferably 2 mm or more, and further preferably 3 mm or more. Moreover, an upper limit of the apparent thickness is not particularly limited, but when the nonwoven fabric 10 is used as the topsheet of the absorbent article, from a viewpoint of providing the topsheet with excellent portability or the like, the apparent thickness is preferably 10 mm or less, more preferably 9 mm or less, and further preferably 8 mm or less.

The basis weight of the nonwoven fabric 10 as a whole having the above-described apparent thickness is preferably 100 g/m$^2$ or less, more preferably 60 g/m$^2$ or less, and further preferably 40 g/m$^2$ or less. Moreover, a lower limit of the basis weight is not particularly limited, but from a viewpoint of securing the texture of the nonwoven fabric, the basis weight is preferably 8 g/m$^2$ or more, more preferably 10 g/m$^2$ or more, and further preferably 15 g/m$^2$ or more.

<Measuring Method of Apparent Thickness of Nonwoven Fabric>

A measuring object nonwoven fabric is cut to 10 cm×10 cm. When an area of 10 cm×10 cm is unable to be taken, the nonwoven fabric is cut to a largest possible area. A thickness at a load of 50 Pa is measured by using a laser displacement sensor head (high-precision displacement sensor ZS-LD80, manufactured by OMRON Corporation). Measurement is carried out in three places, and an average value is taken as the apparent thickness.

In thickness direction of the nonwoven fabric 10, the height H1 of the longitudinal ridge portion 11, the height H2 of the transverse ridge portion 21, and the height h1 of the convex portion 34 in the protruded line portion 31 and the height h2 of the concave portion 35 can be measured by applying mutatis mutandis this measuring method. Moreover, the width Q1 of the thin part 37 in the protruded line portion 31 on the side of the opposite surface Z2, and the width Q2 of the thick part 38 as mentioned above can be measured in the plane view from the side of the opposite surface Z2 by applying mutatis mutandis the above-described measuring method.

<Measuring Method of Basis Weight of Nonwoven Fabric>

A measuring object nonwoven fabric is cut to 10 cm×10 cm. When an area of 10 cm×10 cm is unable to be taken, the nonwoven fabric is cut to a largest possible area. Weight is measured by using a balance, and a measured value is divided by an area of the nonwoven fabric, and the resultant value is taken as basis weight.

When the measuring object nonwoven fabric is taken from a commercially available absorbent article and the like, a measuring object nonwoven fabric is peeled carefully by solidifying an adhesive used in the absorbent article by using a cooling means such as a cold spray, and the resultant sample is measured. In this case, the adhesive is removed by using an organic solvent. This means is the same as all on the measurement of other nonwoven fabrics in the description.

Further, a space surrounded by the longitudinal ridge portion 11 and the transverse ridge portion 21 is opened on a side of the one surface Z1. Thus, a body of a person pressing the nonwoven fabric, for example, a skin surface of the finger can be partially entered in the space. Thus, when the nonwoven fabric 10 is pressed from a side of the one surface Z1, together with sinking cushioning properties of the top portion region 11T, a more airy feeling can be obtained in a part of the above-described space, and as is preferable. Furthermore, a three-dimensional effect is visually produced by opening, and the texture seems to be good also psychologically. Further, upon use as the topsheet of the absorbent article, the opening evokes a height of air permeability to give comfort. Furthermore, the space is kept to form a passage of air, and the air permeability is actually satisfactory to suppress stuffiness.

The fiber amount in the top portion region 31T on a side of the opposite surface Z2 is preferably smaller than the fiber amount in the top portion region 11T on the side of the one surface Z1. Thus, a larger amount of fibers is provided on a top surface to be touched, and smooth texture is felt. On the other hand, the fibers on the top surface can be further increased by arranging a minimum amount of fibers capable of keeping the shape on a back surface not touched. Further, the fibers do not inhibit absorption to efficiently absorb a liquid by decreasing the fibers on the back surface upon using the nonwoven fabric in the topsheet of the sheet. Furthermore, the air permeability can also be improved.

Next, one preferred example of a method for producing the nonwoven fabric 10 is described below, referring to FIGS. 13 to 15.

In the method for producing the nonwoven fabric 10, a support male material 120 shown in FIG. 13(A) and a support female material 130 shown in FIG. 13(B) are used in order to shape a fiber web 110 before being processed into the nonwoven fabric. At this time, in the support male material 120, projections 121 are arranged in one direction and in a direction perpendicular thereto at an interval. On the other hand, in the support female material 130, projections 131 are continued in one direction. The projections 121 of the support male material 120 and the projections 131 of the support female material 130 have a form in which both can be loosely inserted thereinto without interfering each other (see also FIG. 14(A)).

As shown in FIG. 13(C), the fiber web 110 is placed on the support male material 120 and pushed, and interposed with the support female material 130 from above the fiber web 110 to shape the fiber web 110.

The support male material 120 has a plurality of projections 121 in corresponding to positions in which the valley portions 14 surrounded by the longitudinal ridge portions 11 and 11 and the transverse ridge portions 21 and 21 in the nonwoven fabric 10 are shaped. A place between the projections 121 and 121 is formed into a support concave portion 122 in corresponding to a position in which the top portion region 11T of the longitudinal ridge portion 11 on a side of the one surface Z1 is shaped. Thus, the support male material 120 has a concavo-convex shape, and the projections 121 and the support concave portions 122 are alternately arranged in different directions in the plane view. A support bottom portion 123 of the support concave portion 122 has a structure through which hot air is blown, and a plurality of holes is arranged (not shown), for example. For example, as a support for producing the nonwoven fabric 10, directions corresponding to the Y direction and the X direction of the nonwoven fabric 10 are a machine direction and a crosswise direction perpendicular to the machine direction. However, the "different directions" vary depending on the concavo-convex structure of the nonwoven fabric according to the present invention, and are not limited to the Y direction and the X direction. In order to further effectively blow hot air, the support male material 120 corresponding to the support concave portion 122 can also be perforated. A height of the projection 121 of the support male material 120 constitute a factor of determining thickness of the nonwoven fabric 10, and therefore the height of the projection 121 is preferably 3 mm or more, more preferably 5 mm or more, and further preferably 7 mm or more. If the height is equal to or more than this lower limit, the nonwoven fabric 10 having a higher cushion feeling can be produced. The projection 121 may be in a prismatic column or column. In the plane view, the projection 121 is drawn as a square shape relative to a machine direction (MD direction) of the nonwoven fabric 10 in Figures, but the projection 121 may be in a rhombus. From viewpoints of further entering of the fibers into the support male material 120, the shape of the nonwoven fabric 10 being kept and thickness of the nonwoven fabric 10 being easily formed, it is preferable that a shape of the projection 121 is the prismatic column and the shape viewed from the top surface is square. From a viewpoint of facilitating to keep the shape in a finished nonwoven fabric 10, an area of one top surface of the projection 121 in the plane view is preferably 3 mm$^2$ or more. Moreover, the adjacent projections 121 of the support male material 120 are preferably separated from each other by 2 mm or more in the plane view because a space into which the fibers are effectively pushed is secured.

The support female material 130 has the projections 131 that correspond to the support concave portions 122 of the support male material 120, and are continued in one direction in the plane view. A place between the projections 131 and 131 is formed into the support concave portion 132 that corresponds to the projections 121 of the support male material 120, and is continued in the one direction. Thus, the support female material 130 has the concavo-convex shape, and the projections 131 and the support concave portions 132 are alternately arranged in the support female material 130. A support bottom portion 133 of the support concave portion 132 has a structure through which hot air is blown, and for example, a plurality of holes is arranged. A distance between the projections 131 and 131 is adjusted to be larger than the width of the projection 121 of the support male material 120. The distance is appropriately set so that a wall portion in which the fiber web 110 is interposed by the projection 121 of the support male material 120 and the projection 131 of the support female material 130 and the fibers are oriented in thickness direction can be preferably shaped. With regard to a length of the projection 131 of the support female material 130 to be pushed thereinto, the projection 131 preferably has a length of 1 mm or more because the projection 131 is required to be inserted between the projections 121 of the support male material 120. Moreover, as an adjacent pitch of the projections 131 of the support female material 130 to be pushed thereinto, a space into which the fibers are pushed is required in a length over one projection 121 of the support male material 120, and therefore the length is preferably a level formed by adding 1 mm or more to the length of one side on the top surface of the projection 121 of the support male material 120 in the plane view. In addition, when a shape of the top surface of the projection 121 is circular or oval, the above-described length of one side on the top surface of the projection 121 is taken as a diameter or a length of a major axis.

First, in the producing method described above, fiber web 110 before being fused is supplied from a carding machine (not shown) to an apparatus for shaping the web so as to have a predetermined thickness.

Next, as shown in FIG. 13(C), the fiber web 110 containing the thermoplastic fibers is arranged on the support male material 120, and the support female material 130 is pushed into the support male material 120 from above the fiber web 110. At this time, the projections 121 of the support male material 120 are inserted into the support concave portions 132 of the support female material 130. Moreover, the projections 131 of the support female material 130 are inserted into the support concave portions 122 of the support male material 120. Thus, the fibers are oriented in thickness direction and plane direction. Moreover, the support female material 130 is not entered into a part corresponding to the support concave portion 132 of the support female material 130 in the support concave portion 122 between the projections 121 and 121 of the support male material 120. However, the fiber web 110 is interposed between the projections 131 on both ends of the support female material 130, and therefore the fibers on the support concave portion 122 are stretched, and the orientation of the fibers is changed. In ordinary fibers oriented in one direction in which the projection 131 is extended, the fibers in the support concave portion 122 are pulled, and the orientation is changed. The fiber web 110 for the nonwoven fabric in which the orientation is changed if viewed from the top surface can be prepared herein.

As shown in FIG. 14(B), the projections 121 of the support male material 120 are inserted into the support concave portions 132 of the support female material 130. Thus, a fiber layer corresponding to a bottom portion of the above-described region surrounding the portions is shaped. Moreover, the fibers are oriented in plane direction between the bottom portions of the support concave portions 122 and the top portions of the projection 131. The projection 131 inhibits hot air, and therefore fusion is small in the fiber layer to be formed, and a smooth fiber layer is realized. Thus, the fiber layer corresponding to the top portion region 11T of the longitudinal ridge portion 11 on a side of the one surface Z1 is shaped.

Next, the support female material 130 inserted into the support male material 120 is removed, and as shown in FIG. 15, hot air W at a temperature at which each fiber in the fiber web 110 can be properly fused is blown to further fuse the fibers with each other. In this case, the hot air W is blown to the fiber web 110 from the side serving as the opposite surface in the nonwoven fabric 10. A temperature of the hot air W at this time is preferably higher by 0° C. or more and 70° C. or less, and more preferably higher by 5° C. or more and 50° C. or less, than the melting point of thermoplastic fibers constituting the fiber web 110 with consideration of common fiber materials used for products of this type.

The air speed of the hot air W is, although the setup depends on the height of the projection 121 of the support male material 120, preferably 2 m/s or more, and more preferably 3 m/s or more. Thus, satisfactory heat transfer to the fibers is achieved to fuse the fibers with each other, and satisfactory fixing of the concavo-convex shape can be achieved. Moreover, the air speed of the hot air W is preferably 100 m/s or less, and more preferably 80 m/s or less. Thus, the texture of the nonwoven fabric 10 can be improved by suppressing excessive heat transfer to the fibers.

In addition, the fibers not fused are not entangled by reducing the surface roughness of the support female material, and the support female material 130 can be removed in a step of blowing the hot air W. That is, the support male material 120 is inserted into the support female material 130 after preparing the web, the support female material 130 is directly removed, and treatment can be applied thereto by the above-described hot air W. Thus, simpler processing can be achieved. Moreover, in the embodiment, the surface to which hot air is blown during production is taken as the side of the opposite surface Z2, but such a configuration may be formed in which hot air is blown from a side of the one surface Z1, and the number of fused points between the fibers on a side of the one surface Z1 becomes large.

As the thermoplastic fibers, the thermoplastic fibers ordinarily used in a raw material of the nonwoven fabric can be adopted without particular restriction. For example, the thermoplastic fibers may be fibers comprising single resin component, conjugate fibers comprising a plurality of resin components, or the like. Specific examples of the conjugate fibers include a sheath-core type and a side-by-side type.

When conjugate fibers comprising a low-melting component and a high-melting component (for example, sheath-core type conjugate fibers in which the sheath is low-melting component and the core is high-melting component) is used as the thermoplastic fibers, a temperature of the hot air to be blown onto the fiber web 110 is preferably equal to or higher than a melting point of the low-melting component and less than a melting point of the high-melting component. The temperature is more preferably equal to or higher than the melting point of the low-melting component and lower by 10° C. than the melting point of the high-melting component, and further preferably higher by 5° C. or more than the melting point of the low-melting component and lower by 20° C. or more than the melting point of the high-melting component. Moreover, from a viewpoint of moderate elasticity and shape-retaining properties, as an amount of the core being the high-melting component of sheath-core type conjugate fibers is larger, the elasticity is higher. Therefore, a case where an amount of the core component is larger in a cross-sectional area proportion is preferable. Specific examples of the sheath-core type conjugate fibers in which the sheath is a low-melting component and the core is a high-melting component include sheath-core type conjugate fibers in which the sheath is polyethylene (PE) and the core is polyethylene terephthalate (PET).

Further, in the sheath-core type conjugate fibers, in the case where the sheath resin component has lower glass transition temperature than the core resin component (hereinafter, referred to as low glass transition temperature resin) (for example, the core resin component is PET and the sheath resin component is PE), recoverability of thickness of the nonwoven fabric can be enhanced by reducing the mass ratio of the low glass transition temperature resin component. As factors that contribute to this situation, the following factors can be considered. It is known that a low glass transition temperature resin has low relaxation modulus. Moreover, it is also known that recover to the deformation is hard to occur when the relaxation modulus is low. Therefore, it is considered that higher thickness recoverability can be provided to the nonwoven fabric by reducing the low glass transition temperature resin component as much as possible.

In the case of the sheath-core type conjugate fibers, a proportion of the low glass transition temperature resin component (PE and the like) with respect to the total fiber mass is preferably smaller than a proportion of the resin component having high glass transition temperature (PET and the like) with respect to the total fiber mass, by mass ratio. Specifically, the proportion of the low glass transition temperature resin component with respect to the total fiber mass is preferably 45 mass % or less, and more preferably 40 mass % or less, by mass ratio. Thickness recoverability of the nonwoven fabric can be enhanced by reducing the proportion of the low glass transition temperature resin component. Moreover, from a viewpoint of producing the nonwoven fabric, the proportion is preferably 10 mass % or more, and more preferably 20 mass % or more, by mass ratio.

This can also be seen from a graph shown in FIG. 16. FIG. 16 shows recoverability rate after one day compression of a nonwoven fabric in the case of changing the proportion of the core resin component (PET) and the sheath resin component (PE) (measuring method is based on the method shown in the [Method for evaluating recoverability after one day compression] shown in Examples described below). In addition, this nonwoven fabric was measured according to a nonwoven fabric shown in FIG. 6. The nonwoven fabric can be prepared by conditions in Example 2 except fiber conditions. The apparent thickness of the prepared nonwoven fabric was 6.0 mm for a type of "core ratio of 30", 6.9 mm for a type of "core ratio of 50", 6.6 mm for a type of "core ratio of 70", and 6.0 mm for a type of "core ratio of 90". As the proportion of the sheath resin component being PE having low glass transition temperature is smaller (the proportion of the core resin component is larger), the recoverability rate after one day compression is higher. In particular, when the proportion of the sheath resin component becomes less than 50 mass % (the proportion of the core resin component becomes more than 50 mass %), the recoverability rate after one day compression becomes 70% or more, and as is preferable.

In the nonwoven fabric 10 obtained, a surface on a lower side in FIG. 15 is a side of the one surface Z1, and a surface on a side opposite thereto serves as the side of the opposite surface Z2. More specifically, a side of the one surface Z1 in the nonwoven fabric 10 is a side on which the support male material 120 is arranged, and the side of the opposite surface Z2 is a side to which the hot air W is blown. Therefore, the number of fused points between the fibers in the top portion region 31T on the side of the opposite surface Z2 becomes larger than the number of fused points between the fibers the top portion region 11T on a side of the one surface Z1 from a difference in an amount of blowing the hot air W. Further, a surface of the top portion region 11T on a side of the one surface Z1 is formed into a less rough-surface feeling and better texture than a surface of the top portion region 31T on the side of the opposite surface Z2 from a difference in heat quantity. Moreover, the same effect is obtained by a distance from the hot air W. Furthermore, the fibers in the top portion region 31T on the side of the opposite surface Z2 are pulled by inserting the support male material 120 into the support female material 130 by forming a state in which the fiber web 110 is interposed therebetween further toward the support male material 120. Therefore, the fiber amount in the top portion region 31T on the side of the opposite surface Z2 shaped in a top portion of the projection 121 of the support male material 120 becomes smaller than the fiber amount in the top portion region 11T on a side of the one surface Z1 shaped in the bottom portion of the support concave portion 122 of the support male material 120.

The nonwoven fabric 10(10A-10C) described in the embodiments can be applied to a topsheet of an absorbent article such as a sanitary napkin or a disposable diaper, for example. When the nonwoven fabric 10 is used as a topsheet, the nonwoven fabric 10 may be used by directing any surface toward a wearer's skin surface. However, from a viewpoint of the fiber orientation direction, the nonwoven fabric 10 is more preferably used by directing a side of the one surface Z1 toward a wearer's skin surface side. On the other hand, from viewpoints of capability of obtaining the soft texture and further securing the air permeability, the nonwoven fabric 10 is more preferably used by directing the side of the opposite surface Z2 toward the wearer's skin surface side.

Next, as one preferred embodiment of the absorbent article in which the nonwoven fabric according to the present invention is used for the topsheet will be described below, referring to FIG. 17, an example of application to an absorbent main body 204 of a diaper 200. The diaper shown in the figure is a tape-type disposable diaper for infants, and is shown in a state in which the diaper in a flatly unfolded state is a little bent and is viewed from the inside (the skin-contact surface side).

As shown in FIG. 17, an absorbent main body 204 used in a diaper 200 according to the present invention has the following basic configuration. Accordingly, the diaper 200 has a fluid-permeable topsheet 201 disposed on the skin-contact surface side, a fluid-hardly-permeable backsheet 202 disposed on the skin non-contact surface side, and an absorbent body 203 having fluid retainability interposed between the topsheet 201 and the backsheet 202 described above.

As the topsheet 201, the nonwoven fabrics 10 in the above embodiments are applied. The backsheet 202, in the unfolded state, has a shape with its both side edges being constricted inside at the central portion C in the longitudinal direction, and may have a single sheet or a plurality of sheets. In the embodiment, lateral leakage prevention gathers 206 formed by the side sheets 205 are provided. In addition, in FIG. 17, the arrangement and boundaries of each component are not strictly shown, and a structure thereof is not limited as long as it is a common form for diapers of this type.

The above diaper 200 is of a tape type, and a fastening tape 207 is provided at a flap portion on the rear side R. The fastening tape 207 is attached to a tape attachment portion (not shown) provided on the flap portion on the abdomen side F, whereby the diaper can be worn and fixed. At this time, the central portion C of the diaper is gently bent inwards, with the absorbent body 203 extending from the hip portion to the lower abdomen. The diaper can exhibit soft texture and flexible texture by applying the nonwoven fabric 10 as the topsheet 201.

As a shape of an absorbent body 204, the absorbent body 204 has a vertically long shape having the longitudinal direction to be arranged from a lower abdomen side to a hip side through a wearer's crotch part during wearing and the crosswise direction perpendicular thereto. In the specification, a direction having a relatively large length in the plane view of the absorbent main body 204 is referred to as the longitudinal direction, and a direction perpendicular thereto is referred to as the crosswise direction. The above-described longitudinal direction typically corresponds to a front-back direction of a human body in a worn state.

It is preferable that the topsheet 201 is formed of the above-mentioned nonwoven fabric 10 of the present invention, and is a hydrophilic nonwoven fabric. As the hydrophilic nonwoven fabric, fibers in which the fibers are conjugate fibers of polypropylene and polyethylene, conjugate fibers of polyethylene terephthalate and polyethylene or the like, and are subjected to hydrophillisation treatment can be preferably used.

As the backsheet 202 and the absorbent body 203, for example, materials described in JP-A-2013-147784, JP-A-2014-005565 and the like can be used.

As the topsheet 201 of the diaper 200, in the nonwoven fabric 10 of the present invention, the fiber orientation of the longitudinal ridge portion 11 and the fiber orientation of the transverse ridge portion 21 are directed toward the extending direction of each ridge portion, thereby forming a material having excellent texture.

The nonwoven fabric of the present invention can be used for a variety of uses. For example, the nonwoven fabric can be suitably used as the topsheet of the absorbent article such as a disposable diaper for an adult or for an infant, a sanitary napkin, a panty liner, a urine pad and the like. Further, the nonwoven fabric can be also used in the form of a sublayer to be interposed between a topsheet and an absorbent body of a sanitary item, a diaper or the like, a covering sheet (core-wrapping sheet) of the absorbent body, or the like. Furthermore, the nonwoven fabric can be also used in a wiping sheet for cleaning.

With regard to the above embodiments, the present invention further discloses nonwoven fabrics and absorbent articles described below.

<1>

A nonwoven fabric, comprising one surface and an opposite surface on a side opposite to the one surface for top and back surfaces of the nonwoven fabric, wherein, on a side of the one surface, a plurality of longitudinal ridge portions protruding on the side of the one surface in thickness direction of the nonwoven fabric is extended in one direction on the side of the one surface in a plane view, and is aligned at intervals on the side of the one surface in the plane view, in other direction, different from the one direction on the side of the one surface, transverse ridge portions extending in the other direction on the side of the one surface are arranged by linking the longitudinal ridge portions, and a fiber orientation direction in the longitudinal ridge portions is different from a fiber orientation direction in the transverse ridge portions.

<2>

The nonwoven fabric according to the above item <1>, wherein, on a side of the opposite surface, the nonwoven fabric comprises: a plurality of protruded line portions that is extended in one direction on the side of the opposite surface in a plane view, and is aligned at intervals on the side of the opposite surface, in other direction, different from the one direction on the side of the opposite surface; and recessed line portions interposed between the plurality of protruded line portions, in which the recessed line portions are extended in the one direction on the side of the opposite surface.

<3>
The nonwoven fabric according to the above item <2>, wherein the protruded line portions are formed by connecting a plurality of convex portions in a ridge line-like shape.

<4>
The nonwoven fabric according to the above item <2> or <3>, wherein, in the protruded line portions, thin parts and thick parts in the plane view are alternately linked and arranged.

<5>
The nonwoven fabric according to any one of the above items <1> to <4>, wherein, on a side of the opposite surface, the nonwoven fabric comprises: a plurality of protruded line portions that is extended in one direction on the side of the opposite surface in a plane view, and is aligned at intervals in other direction on the side of the opposite surface, in which the other direction is different from the one direction on the side of the opposite surface; and recessed line portions interposed between the plurality of protruded line portions, in which the recessed line portions are extended in the one direction on the side of the opposite surface, and wherein the protruded line portions are formed by connecting a plurality of convex portions in a ridge line-like shape, in which thin parts and thick parts in the plane view are alternately linked and arranged.

<6>
A nonwoven fabric, comprising one surface and an opposite surface on a side opposite to the one surface for top and back surfaces of the nonwoven fabric, wherein, on a side of the opposite surface, the nonwoven fabric comprises: a plurality of protruded line portions that is extended in one direction on the side of the opposite surface in a plane view, and is aligned at intervals in other direction on the side of the opposite surface, in which the other direction is different from the one direction on the side of the opposite surface; and recessed line portions interposed between the plurality of protruded line portions, in which the recessed line portions are extended in the one direction on the side of the opposite surface, and wherein the protruded line portions are formed by connecting a plurality of convex portions in a ridge line-like shape, in which thin parts and thick parts in the plane view are alternately linked and arranged.

<7>
The nonwoven fabric according to the above item <6>, wherein, on a side of the one surface, a plurality of longitudinal ridge portions protruding on the side of the one surface in thickness direction of the nonwoven fabric is extended in one direction on the side of the one surface in a plane view, and is aligned at intervals in other direction on the side of the one surface in the plane view, in which the other direction is different from the one direction on the side of the one surface.

<8>
The nonwoven fabric according to the above item <7>, wherein transverse ridge portions extending in the other direction on the side of the one surface are arranged by linking the longitudinal ridge portions.

<9>
The nonwoven fabric according to the above item <8>, wherein a fiber orientation direction in the longitudinal ridge portions is different from a fiber orientation direction in the transverse ridge portions.

<10>
The nonwoven fabric according to any one of the above items <1> to <5> and <9>, wherein by "the fiber orientation direction is different" is meant that both orientation directions obtained according to the following [Method for measuring fiber orientation parameter] are different by 5° or more:

[Method for Measuring Fiber Orientation Parameter]

a nonwoven fabric is cut into a square of 2 cm×2 cm, a cut piece is applied as a sample, and observed from the side of the one surface Z1; a scanning electron microscope (SEM) is preferably used to the observation, for example; as the SEM, JCM-6100Plus (manufactured by JEOL Ltd.) is used, for example; in SEM observation, vapor deposition treatment is preferably applied to the sample in advance by a recommended method; a center of the longitudinal ridge portion is magnified at a magnification of 50 times, and is shown in a center of an observation screen; next, a square having a length of 500 µm in one side with the center of the screen as an intersection of diagonal lines is drawn to be in parallel to the longitudinal ridge portion, and the number of fibers passing through two sides on both sides in parallel to an extending direction of the longitudinal ridge portion is counted (taken as the fiber number N1); moreover, in the same manner, the number of fibers passing through two sides intersected vertically to the extending direction of the longitudinal ridge portion is counted (taken as the fiber number N2); the fiber orientation parameter in the longitudinal ridge portion is determined based on the following (Formula 1);

Fiber orientation parameter of longitudinal ridge portion (%)={Fiber number $N2$/(Fiber number $N1$+Fiber number $N2$)}×100  (Formula 1)

such measurement is carried out on three arbitrary places, and measured values are averaged; when an average of fiber orientation parameters is more than 50%, the fibers in the region are judged to be oriented in the same direction with the extending direction of the longitudinal ridge portion, and the direction is taken as an orientation direction; a larger numerical value indicates that the fibers are strongly oriented in the same direction with the extending direction of the longitudinal ridge portion;

when a fiber orientation parameter in the transverse ridge portion is measured, in the same manner described above, a center of the transverse ridge portion is magnified at a magnification of 50 times, and is shown in a center of an observation screen; next, a square having a length of 500 µm in one side with the center of the screen as an intersection of diagonal lines is drawn to be in parallel to the longitudinal ridge portion, and the number of fibers passing through two sides on both sides in parallel to an extending direction of the longitudinal ridge portion is counted (taken as the fiber number N1); moreover, in the same manner, the number of fibers passing through two sides intersected vertically to the extending direction of the longitudinal ridge portion is counted (taken as the fiber number N2); the fiber orientation parameter in the transverse ridge portion with reference to the extending direction of the longitudinal ridge portion is determined based on the (Formula 1);

in order to judge whether or not the fibers in the transverse ridge portion are oriented in the same direction with the extending direction of the transverse ridge portion, a square is drawn to be in parallel to the transverse ridge portion, and not a square in parallel to the longitudinal ridge portion as in the above-described method; the number of fibers passing through two sides on both sides in parallel to the extending direction of the transverse ridge portion is counted (taken as the fiber number N3); moreover, in the same manner, the number of fibers passing through two sides intersected vertically to the extending direction of the transverse ridge portion is counted (taken as the fiber number N4); a fiber orientation parameter (%) along the transverse ridge portion is determined, according to the above-described method, based on the following (Formula 2), and when a value is more than 50%, the fibers are judged to be oriented in the same direction with the extending direction of the transverse ridge portion;

Fiber orientation parameter along transverse ridge portion (%)={Fiber number $N4$/(Fiber number $N3$+Fiber number $N4$)}×100  (Formula 2).

<11>

The nonwoven fabric according to any one of the above items <1> to <5> and <8> to <10>, wherein the plurality of transverse ridge portions is aligned at intervals in the one direction on the side of the one surface.

<12>

The nonwoven fabric according to the above item <11>, comprising a lattice-shaped concavo-convex surface on the side of the one surface by the longitudinal ridge portions and the transverse ridge portions.

<13>

The nonwoven fabric according to any one of the above items <1> to <5> and <8> to <12>, wherein the fiber orientation direction in the longitudinal ridge portions and the fiber orientation direction in the transverse ridge portions are directed toward the extending direction of the ridge portions, respectively.

<14>

The nonwoven fabric according to the above item <13>, wherein by "directed" is meant that the fiber orientation parameter obtained according to the following [Method for measuring fiber orientation parameter] is 50% or more:
[Method for Measuring Fiber Orientation Parameter]

a nonwoven fabric is cut into a square of 2 cm×2 cm, a cut piece is applied as a sample, and observed from the side of the one surface Z1; a scanning electron microscope (SEM) is preferably used to the observation, for example; as the SEM, JCM-6100Plus (manufactured by JEOL Ltd.) is used, for example; in SEM observation, vapor deposition treatment is preferably applied to the sample in advance by a recommended method; a center of the longitudinal ridge portion is magnified at a magnification of 50 times, and is shown in a center of an observation screen; next, a square having a length of 500 μm in one side with the center of the screen as an intersection of diagonal lines is drawn to be in parallel to the longitudinal ridge portion, and the number of fibers passing through two sides on both sides in parallel to an extending direction of the longitudinal ridge portion is counted (taken as the fiber number N1); moreover, in the same manner, the number of fibers passing through two sides intersected vertically to the extending direction of the longitudinal ridge portion is counted (taken as the fiber number N2); the fiber orientation parameter in the longitudinal ridge portion is determined based on the following (Formula 1);

Fiber orientation parameter of longitudinal ridge portion (%)={Fiber number $N2$/(Fiber number $N1$+Fiber number $N2$)}×100  (Formula 1)

such measurement is carried out on three arbitrary places, and measured values are averaged; when an average of fiber orientation parameters is more than 50%, the fibers in the region are judged to be oriented in the same direction with the extending direction of the longitudinal ridge portion, and the direction is taken as an orientation direction; a larger numerical value indicates that the fibers are strongly oriented in the same direction with the extending direction of the longitudinal ridge portion;

when a fiber orientation parameter in the transverse ridge portion is measured, in the same manner described above, a center of the transverse ridge portion is magnified at a magnification of 50 times, and is shown in a center of an observation screen; next, a square having a length of 500 μm in one side with the center of the screen as an intersection of diagonal lines is drawn to be in parallel to the longitudinal ridge portion, and the number of fibers passing through two sides on both sides in parallel to an extending direction of the longitudinal ridge portion is counted (taken as the fiber number N1); moreover, in the same manner, the number of fibers passing through two sides intersected vertically to the extending direction of the longitudinal ridge portion is counted (taken as the fiber number N2); the fiber orientation parameter in the transverse ridge portion with reference to the extending direction of the longitudinal ridge portion is determined based on the (Formula 1);

in order to judge whether or not the fibers in the transverse ridge portion are oriented in the same direction with the extending direction of the transverse ridge portion, a square is drawn to be in parallel to the transverse ridge portion, and not a square in parallel to the longitudinal ridge portion as in the above-described method; the number of fibers passing through two sides on both sides in parallel to the extending direction of the transverse ridge portion is counted (taken as the fiber number N3); moreover, in the same manner, the number of fibers passing through two sides intersected vertically to the extending direction of the transverse ridge portion is counted (taken as the fiber number N4); a fiber orientation parameter (%) along the transverse ridge portion is determined, according to the above-described method, based on the following (Formula 2), and when a value is more than 50%, the fibers are judged to be oriented in the same direction with the extending direction of the transverse ridge portion;

Fiber orientation parameter along transverse ridge portion (%)={Fiber number $N4$/(Fiber number $N3$+Fiber number $N4$)}×100  (Formula 2).

<15>

The nonwoven fabric according to any one of the above items <1> to <5> and <8> to <14>, wherein a height of the longitudinal ridge portion and a height of the transverse ridge portion are different.

<16>

The nonwoven fabric according to any one of the above items <1> to <5> and <8> to <15>, wherein a height of the longitudinal ridge portion is higher than a height of the transverse ridge portion.

<17>

The nonwoven fabric according to any one of the above items <1> to <5> and <8> to <16>, wherein the transverse ridge portions are bent in thickness direction of the nonwoven fabric.

<18>

The nonwoven fabric according to any one of the above items <1> to <5> and <8> to <17>, wherein the transverse ridge portions are bent into a concave form.

<19>
The nonwoven fabric according to any one of the above items <1> to <5> and <8> to <18>, wherein the transverse ridge portions are arranged in a bent state in such a manner that the transverse ridge portions are recessed in the direction on the side of the opposite surface between the longitudinal ridge portions.
<20>
The nonwoven fabric according to any one of the above items <2> to <9>, wherein each of two lines forming a profile of the protruded line portion in the crosswise direction in the plane view from the side of the opposite surface is a curve having a plurality of arcs.
<21>
The nonwoven fabric according to any one of the above items <2> to <9>, comprising fluff on the side portion of the protruded line portion.
<22>
The nonwoven fabric according to any one of the above items <2> to <9>, wherein by "comprising the fluff" is meant that the fluff is in a state in which one end of the fibers, which are not fused, comes out from the protruded line portions.
<23>
The nonwoven fabric according to any one of the above items <3> to <9>, wherein by "the plurality of convex portions is connected in a ridge line-like shape" is meant that concave portions recessed in thickness direction are arranged between the plurality of convex portions.
<24>
The nonwoven fabric according to any one of the above items <2> and <4> to <9>, wherein the one direction on the side of the one surface coincides with the one direction on the side of the opposite surface.
<25>
The nonwoven fabric according to any one of the above items <1> to <24>, wherein an apparent thickness of the nonwoven fabric is 1.5 mm or more and 10 mm or less, preferably 2 mm or more, and more preferably 3 mm or more; and preferably 9 mm or less, and more preferably 8 mm or less.
<26>
The nonwoven fabric according to any one of the above items <1> to <24>, wherein an apparent thickness of the nonwoven fabric is 3 mm or more and 8 mm or less.
<27>
The nonwoven fabric according to any one of the above items <1> to <26>, wherein a basis weight of the nonwoven fabric as a whole is 8 g/m² or more and 100 g/m² or less, preferably 60 g/m² or less, and more preferably 40 g/m² or less; and preferably 10 g/m² or more, and more preferably 15 g/m² or more.
<28>
An absorbent article comprising the nonwoven fabric according to any one of the above items <1> to <27>.
<29>
An absorbent article, wherein the side of the one surface of the nonwoven fabric according to any one of the above items <1> to <27> is arranged toward a skin-contact surface side, and is used as the topsheet.
<30>
An absorbent article, wherein the side of the one surface of the nonwoven fabric according to any one of the above items <1> to <27> is arranged toward a skin non-contact surface side, and is used as the topsheet.
<31>
The absorbent article according to any one of the above items <28> to <30>, wherein the one direction on the side of the one surface or the one direction on the side of the opposite surface coincides with longitudinal direction of the absorbent article.

EXAMPLES

Hereinafter, the present invention will be described more in detail with reference to Examples, but the present invention is not limited thereto. The item "-" in the following Table means that there are no values corresponding to the item and the like.

Example 1

A fiber web was prepared by using a sheath-core type (polyethylene terephthalate (PET) (core):polyethylene (PE) (sheath)=5:5 (mass ratio)) thermoplastic fibers having a fineness of 1.8 dtex. As shown in FIG. 13, the fiber web was arranged on a support male material 120, and a support female material 130 was pushed into the support male material 120 from above the fiber web 110 to perform shaping processing thereto. Subsequently, the support female material 130 was removed, and fusion processing was performed by blowing hot air W to prepare a nonwoven fabric shown in FIG. 1. At this time, as the support male material 120, a material in which a height of a projection 121 was adjusted to 8 mm to have a prismatic column shape, and a square shape of 2 mm×2 mm when viewed from a top surface was used. A pitch of a prismatic column was adjusted to 5 mm in an MD direction and a CD direction, respectively. As the support female material 130, a material having straight line-shaped projections 131 each having a width of 2 mm and made of metal was used, and the support female material 130 was pushed between the projections 121 of the support male material 120. Between adjacent projections 121 and 121 of the support female material 130, the projections 121 were arranged at a pitch of 5 mm, and a space into which fibers when the support male material 120 are pushed into the support female material 130 were entered was 0.5 mm on one side, and was 1 mm in combining the spaces on both sides of the projection 120 of the support male material 120. The resultant material was taken as a nonwoven fabric sample in Example 1. Blowing treatment by hot air was performed under conditions of a temperature of 160° C., an air speed of 6 m/s, and a blowing time of 6 s.

The nonwoven fabric sample in Example 1 had a fineness of 1.8 dtex. The nonwoven fabric sample in Example 1 had longitudinal ridge portions and transverse ridge portions, in which an extending direction of the longitudinal ridge portion and an extending direction of the transverse ridge portion were in a direction perpendicular to each other. Moreover, as is found from an orientation parameter shown in Table 1, a fiber orientation direction in the longitudinal ridge portion and a fiber orientation direction in the transverse ridge portions are in directions in which the longitudinal ridge portion and the transverse ridge portion were extended, respectively, and in directions perpendicular to each other (different directions).

Example 2

A nonwoven fabric shown in FIG. 6 was prepared by applying the same fiber web with the material in Example 1 as a male material and setting the male material in a reverse direction for MD and CD. All were the same with the conditions in Example 1 except the setting. The resultant material was taken as a nonwoven fabric sample in Example 2.

Example 3

A nonwoven fabric shown in FIG. 7, in which the nonwoven fabric sample in Example 1 was turned upside down, was prepared, and the resultant nonwoven fabric was taken as a nonwoven fabric sample in Example 3. Therefore, a fiber orientation direction in a longitudinal ridge portion and a fiber orientation direction in a transverse ridge portion were in directions in which the longitudinal ridge portion and transverse ridge portion were extended, respectively, and in directions perpendicular to each other (different directions), on a side of the one surface Z1 in the same manner as in Example 1.

Example 4

A nonwoven fabric sample in Example 4 was prepared according to the same producing method as in Example 1 except that thermoplastic fibers of a sheath-core type (polyethylene terephthalate (PET) (core):polyethylene (PE) (sheath)=7:3 (mass ratio)) and having a fiber diameter of 3.2 dtex were used.

Comparative Example 1

A nonwoven fabric shown in FIG. 1 in JP-A-2012-136790 was prepared by using thermoplastic fibers having a fineness of 1.8 dtex according to the production method described in the same gazette, and the resultant nonwoven fabric was taken as a nonwoven fabric sample in Comparative Example 1.

Comparative Example 2

A flat nonwoven fabric without concavo-convex shaping was prepared by using thermoplastic fibers having a fiber diameter of 1.8 dtex according to an air-through production method, and the resultant material was taken as a nonwoven fabric sample in Comparative Example 2.

Comparative Example 3

A flat nonwoven fabric used in a surface material of Merries Pants L size, manufactured by Kao Corporation, 2016, was peeled, and the resultant material was taken as a nonwoven fabric sample in Comparative Example 3.

Comparative Example 4

A concavo-convex nonwoven fabric used in a surface material of Merries M size, manufactured by Kao Corporation, 2016, was peeled, and the resultant material was taken as a nonwoven fabric sample in Comparative Example 4.

For the Examples and the Comparative Examples described above, a fiber orientation parameter (orientation direction) in each ridge portion, a height H2 of a transverse ridge portion, a width Q1 of a thin part and a width Q2 of a thick part each in a protruded line portion, compression energy WC, compression recovery rate RC, a compressive deformation amount, and texture were determined. Measurement of each measuring item is carried out according to the above-mentioned (Method for measuring compressive deformation amount) and the following measuring methods. With regard to the fiber orientation parameter, a value measured in an arbitrary site as viewed from a top surface was recorded for the sample having no ridge. Moreover, recoverability after one day compression was also evaluated on Examples described above.

[Method for Evaluating Cushioning Properties (Compression Energy WC) and Shape-Retaining Properties (Compression Recovery Rate RC)]

With regard to a method for evaluating cushioning properties and shape-retaining properties, the above-mentioned KES Compression Tester was used. Measurement was carried out under the condition of a temperature of 22° C. and RH of 65%. KES Compression Tester was used to evaluate compression characteristics up to 5.0 kPa in an ordinary mode, and compression energy WC value and a compression recovery rate RC value up to maximum pressure 5.0 kPa was read. As measured values, measurement was carried out on 3 points in the nonwoven fabric, the measured values were averaged, such operation was performed three times, and average values were taken as a WC value and an RC value.

The above-described WC value represents energy required for compression per unit area, and as the WC value is larger, the nonwoven fabric is easily compressed and has high cushioning feeling. Further, as the compressive deformation amount is larger even at the same degree of WC, the nonwoven fabric has moderate elasticity, in which a high cushion feeling is sensed, and texture is satisfactory.

The above-described RC value was expressed by percentage of a ratio of restored energy relative to energy during compression, and a larger RC value is judged to have better restoration properties against compression.

[Method for Evaluating Texture]

The flat nonwoven fabric in Comparative Example 3 was rated as 3 points, and the concavo-convex nonwoven fabric in Comparative Example 4 was rated as 4 points, and based on 10 points, three researchers (twenties to thirties in their age) engaged in research and development of texture of the nonwoven fabric were asked to assume the best texture material in clothes and nonwoven fabrics which have been so far touched, evaluation in 10 grades was conducted, the evaluated values were averaged, and summarized in an integer by rounding off the resultant value to the first decimal place. In assumption of touching a surface material of a diaper, the researchers each touched on a surface of a sample placed on a plane with a dominant hand. The evaluation was conducted directly by visual observation.

[Method for Evaluating Recoverability after One Day Compression]

A nonwoven fabric was sandwiched between two acrylic plates together with a washer having thickness of 0.7 mm, a weight (20 kg) was placed thereon, and a load was applied to compress the nonwoven fabric to thickness of 0.7 mm. After standing for one day in this state, the weight and the acrylic plates were removed from the nonwoven fabric, and after 10 minutes an apparent thickness of the nonwoven fabric was measured. From this measurement value and an apparent thickness of the nonwoven fabric before compression previously measured, recovery rate of thickness of the nonwoven fabric was calculated to evaluate the recoverability after one day compression of the nonwoven fabric.

TABLE 1

|  |  | Example 1 | Example 2 | Example 3 | Example 4 |
|---|---|---|---|---|---|
| Basis weight | g/m² | 29 | 28 | 29 | 31 |
| Apparent thickness | mm | 7.3 | 7.0 | 7.4 | 7.3 |
| Orientation parameter of longitudinal ridge portion | % | 59.0 | 62.0 | — | 63.0 |
| Orientation parameter of transverse ridge portion | % | 58.0 | 52.0 | — | 55.0 |
| Height of transverse ridge portion (H2) | mm | 3.3 | 6.9 | — | 2.8 |
| Width Q1 of thin part of protruded line portion | mm | — | — | 2.0 | — |
| Width Q2 of thick part of protruded line portion | mm | — | — | 3.1 | — |
| Compression energy WC | N · m/m² | 1.14 | 0.98 | 1.56 | 1.18 |
| Compression recovery rate RC | % | 37 | 41 | 39 | 45 |
| Compressive deformation amount | mm | 5.9 | 3.7 | 5.6 | 5.6 |
| Texture | point | 9 | 8 | 9 | 9 |
| Recovery rate after one day compression | % | 52 | 52 | 52 | 74 |

|  |  | Comparative Example 1 | Comparative Example 2 | Comparative Example 3 | Comparative Example 4 |
|---|---|---|---|---|---|
| Basis weight | g/m² | 33 | 98 | 24 | 44 |
| Apparent thickness | mm | 4.0 | 6.0 | 1.0 | 1.4 |
| Orientation parameter of longitudinal ridge portion | % | 47.0 | 60.0 | 60.0 | 55.0 |
| Orientation parameter of transverse ridge portion | % | 45.0 | — | — | — |
| Height of transverse ridge portion (H2) | mm | 3.1 | — | — | — |
| Width Q1 of thin part of protruded line portion | mm | — | — | — | — |
| Width Q2 of thick part of protruded line portion | mm | — | — | — | — |
| Compression energy WC | N · m/m² | 1.00 | 0.95 | 0.09 | 0.20 |
| Compression recovery rate RC | % | 43 | 65 | 56 | 48 |
| Compressive deformation amount | mm | 2.1 | 1.8 | 0.4 | 0.6 |
| Texture | point | 5 | 1 | 3 | 4 |

As shown in Table 1, the nonwoven fabric in Comparative Example 1 had the concavo-convex shape in the same manner as in Examples 1 to 4, but fiber orientation was in the same direction, and the compressive deformation amount was superior in Examples 1 to 4 in which the fiber orientation direction in the longitudinal ridge portions was different from the fiber orientation direction in the transverse ridge portions. The nonwoven fabric in Comparative Example 2 had the apparent thickness equivalent to or more than the level as in Examples, but the shape was flat, and therefore the compressive deformation amount was superior in Examples 1 to 4. The fiber amount in Comparative Example 3 was small at the same degree as in Examples, but the nonwoven fabrics in Examples 1 to 4 had a larger thickness. Moreover, the compressive deformation amount in Examples 1 to 4 was larger than the amount in Comparative Example 3. The nonwoven fabric in Comparative Example 4 had the concavo-convex shape in the same manner as in Examples, but the orientation direction was the same, and therefore the compressive deformation amount was larger in Examples 1 to 4.

As described above, orientation was different between the longitudinal ridge portions and the transverse ridge portions in Examples 1 to 4, and therefore the compressive deformation amount was large, and the texture was felt to be satisfactory by the moderate elasticity and the cushion feeling. Moreover, liquid spreading was also confirmed to be small.

Furthermore, among Examples 1 to 4, the nonwoven fabric in Example 4 in which a mass ratio of PE (temperature of glass transition component is lower in comparison with PET being core resin) being sheath resin was decreased was excellent in recoverability after one day compression, and it was found that the nonwoven fabric in Example 4 have high thickness recoverability even after the nonwoven fabric is compressed with a packing and the like.

Having described our invention as related to this embodiments and Examples, it is our intention that the invention not be limited by any of the details of the description, unless otherwise specified, but rather be construed broadly within its spirit and scope as set out in the accompanying claims.

This application claims priority on Patent Application No. 2017-168002 filed in Japan on Aug. 31, 2017, which is entirely herein incorporated by reference.

DESCRIPTION OF SYMBOLS 10, 10A, 10B, 10C Nonwoven fabric
11 Longitudinal ridge portion
11T Top portion region
11W Wall portion
12 Internal space
14 Valley portion
21 Transverse ridge portion
21T Top portion region 21W Wall portion
22 Internal space
31 Protruded line portion
31T Top portion region
31W Wall portion
32 Internal space
34 Convex portion
35 Concave portion
36 Recessed line portion
37 Thin part
38 Thick part
H1 Height of longitudinal ridge portion
H2 Height of transverse ridge portion
h1 Height of convex portion
h2 Height of concave portion
S Plane
Q1 Width of thin part
Q2 Width of thick part
Z1 A side of the one surface
Z2 A side of the opposite surface

The invention claimed is:

1. A nonwoven fabric, comprising one surface and an opposite surface on a side opposite to the one surface for top and back surfaces of the nonwoven fabric, wherein,
   on a side of the one surface,
   a plurality of longitudinal ridge portions protruding on the side of the one surface in thickness direction of the nonwoven fabric is extended in one direction on the side of the one surface in a plane view, and is aligned at intervals on the side of the one surface in the plane view, in other direction, which is orthogonal to the one direction on the side of the one surface,
   transverse ridge portions extending in the other direction on the side of the one surface are arranged by linking the longitudinal ridge portions,
   wherein the transverse ridge portions immediately adjacent to each other in the direction which is orthogonal to the one direction by interposing a single longitudinal ridge portion are aligned in the same straight-line, and
   a fiber orientation direction in the longitudinal ridge portions is different from a fiber orientation direction in the transverse ridge portions, and
   wherein the fiber orientation direction in the longitudinal ridge portions is directed toward the extending direction of the longitudinal ridge portions and the fiber orientation direction in the transverse ridge portions is directed toward the extending direction of the transverse ridge portions.

2. The nonwoven fabric according to claim 1, wherein, on a side of the opposite surface,
   the nonwoven fabric comprises: a plurality of continuous protruded line portions that extend in one direction on the side of the opposite surface in a plane view, the plurality of protruded line portions is aligned at intervals on the side of the opposite surface in an other direction, different from the one direction on the side of the opposite surface;
   a plurality of continuous recessed line portions is adjacently interposed between the plurality of protruded line portions, wherein the recessed line portions extend in the one direction on the side of the opposite surface;
   wherein widths of protruded line portions and the recessed line portions are not always constant; and
   wherein the recessed line portions adjacently interposed between the protruded line portions form a convex-concave-convex structure.

3. The nonwoven fabric according to claim 2, wherein the protruded line portions are formed by connecting a plurality of convex portions in a ridge line-like shape.

4. The nonwoven fabric according to claim 2, wherein, in the protruded line portions, thin parts and thick parts in the plane view are alternately linked and arranged.

5. The nonwoven fabric according to claim 1, wherein, on a side of the opposite surface,
   the nonwoven fabric comprises: a plurality of protruded line portions that is extended in one direction on the side of the opposite surface in a plane view, and is aligned at intervals in other direction on the side of the opposite surface, in which the other direction is different from the one direction on the side of the opposite surface; and
   recessed line portions interposed between the plurality of protruded line portions, in which the recessed line portions are extended in the one direction on the side of the opposite surface, and
   wherein the protruded line portions are formed by connecting a plurality of convex portions in a ridge line-like shape, in which thin parts and thick parts in the plane view are alternately linked and arranged.

6. The nonwoven fabric according to claim 1, wherein the plurality of transverse ridge portions is aligned at intervals in the one direction on the side of the one surface.

7. The nonwoven fabric according to claim 1, wherein a height of the longitudinal ridge portion and a height of the transverse ridge portion are different.

8. The nonwoven fabric according to claim 1, wherein a height of the longitudinal ridge portion is greater than a height of the transverse ridge portion.

9. The nonwoven fabric according to claim 1, wherein the transverse ridge portions are bent in thickness direction of the nonwoven fabric.

10. The nonwoven fabric according to claim 1, wherein the transverse ridge portions are bent into a concave form.

11. The nonwoven fabric according to claim 2, wherein each of two lines forming a profile of the protruded line portion in the crosswise direction in the plane view from the side of the opposite surface is a curve having a plurality of arcs.

12. The nonwoven fabric according to claim 2, comprising fluff on the side portion of the protruded line portion.

13. The nonwoven fabric according to claim 2, wherein the one direction on the side of the one surface coincides with the one direction on the side of the opposite surface.

14. An absorbent article comprising the nonwoven fabric according to claim 1.

15. An absorbent article, wherein the side of the one surface of the nonwoven fabric according to claim 1 is arranged toward a skin-contact surface side, and is used as a topsheet.

16. An absorbent article, wherein the side of the one surface of the nonwoven fabric according to claim 1 is arranged toward a skin non-contact surface side, and is used as a topsheet.

* * * * *